United States Patent
Kawanishi et al.

(10) Patent No.: US 6,957,167 B2
(45) Date of Patent: Oct. 18, 2005

(54) VISCERAL FAT DETERMINING DEVICE WITH A WEIGHT-MEASURING FUNCTION

(75) Inventors: Shozo Kawanishi, Akashi (JP); Koichi Okita, Akashi (JP)

(73) Assignee: Yamato Scale Co., Ltd., Akashi (JP)

( * ) Notice: Subject to any disclaimer, the term of this patent is extended or adjusted under 35 U.S.C. 154(b) by 20 days.

(21) Appl. No.: 10/343,591

(22) PCT Filed: Aug. 30, 2001

(86) PCT No.: PCT/JP01/07458

§ 371 (c)(1), (2), (4) Date: Jan. 31, 2003

(87) PCT Pub. No.: WO02/17785

PCT Pub. Date: Mar. 7, 2002

(65) Prior Publication Data

US 2003/0167020 A1 Sep. 4, 2003

(30) Foreign Application Priority Data

Aug. 31, 2000 (JP) ...................... 2000-263363

(51) Int. Cl.[7] ............................................. G06F 15/02
(52) U.S. Cl. ...................................... 702/173; 600/547
(58) Field of Search .................. 702/173, 30; 600/300, 600/547

(56) References Cited

U.S. PATENT DOCUMENTS 6,322,504 B1 * 11/2001 Kirshner ..................... 600/300

FOREIGN PATENT DOCUMENTS

| JP | 11-128198 | * | 5/1999 |
| JP | 2000-225100 | * | 8/2000 |
| JP | 2000-350710 | | 12/2000 |

OTHER PUBLICATIONS

International Search Report for PCT/JP01/07458, Sep. 20, 2001.

* cited by examiner

Primary Examiner—Michael Nghiem
Assistant Examiner—Xiuqin Sun
(74) Attorney, Agent, or Firm—Kolisch Hartwell, P.C.

(57) ABSTRACT

A visceral fat determining device with a weight-measuring function which is capable of measuring weight of a subject and providing information associated with the visceral fat of the subject and easy to operate at home or the like is disclosed. The visceral fat determining device with a weight-measuring function 10 includes a weight-measuring device for measuring the weight of a subject when the subject stands on a measuring surface, an input device for inputting personal data representing physical characteristics of the subject, a data processing unit for processing various types of calculations, and a display portion for displaying the personal data and a result of the calculation, wherein quantitative information associated with BMI and the visceral fat of the subject can be obtained by inputting an abdominal girth of the subject which is a circumferential length of a torso of the subject and height of the subject.

31 Claims, 5 Drawing Sheets

Standard Values for Judging Obesity

|  | BMI | Waist Size | Abdominal Visceral Fat Cross Sectional Area |
|---|---|---|---|
| Male | 25 | 85cm | 100cm$^2$ |
| Female | 25 | 90cm | 100cm$^2$ |

VISCERAL FAT DETERMINING DEVICE WITH A WEIGHT-MEASURING FUNCTION

TECHNICAL FIELD

The present invention relates to a visceral fat determining device with a weight measuring function which is capable of measuring the weight of a human subject and providing information on visceral fat which is part of internal body fat of the human body through a simple procedure.

BACKGROUND ART

Conventionally, attention has been paid to the internal body fat content of a person in view of health maintenance. Specifically, since a rise in internal body fat content of a person may increase a risk for the person to get so-called adult diseases, monitoring the internal body fat content of the person may prevent the adult diseases. Body Mass Index (BMI) has been widely used as an index to evaluate the internal body fat content since it can be easily calculated from the height and weight of an individual person.

Another useful index to evaluate the internal body fat content of a person is a body-fat ratio. Recently, various types of body fat meters capable of measuring the body-fat ratio have become available on the market and, with these body fat meters, the body-fat ratio can be easily measured at home or the like.

Among the internal body fats, the visceral fat has been believed to be a factor particularly contributing to various complications of arteriosclerosis, diabetes, and so on. For this reason, the visceral fat content has been becoming an important factor in view of health maintenance.

The BMI and the body-fat ratio described above are information obtained as average data on internal body fat content in the whole body. Hence, even if the result of the BMI or the body-fat ratio does not indicate any health problem, it does not necessarily mean that there is no health problem in relation to the visceral fat content.

Information on the visceral fat can be obtained through a diagnostic method such as abdominal tomography by means of CT scanning, MRI, and so on. This method allows directly observing the abdominal portion itself, thereby making it possible to accurately obtain information on the visceral fat.

Such a method, however, is problematic in that the procedure requires a large-scale apparatus installed in a major hospital, a certain length of time necessary for measurement and data analysis, and highly specific technical knowledge for the procedure and data analysis. Hence, the method is not suitable for use at home or the like to obtain the visceral fat content.

On the other hand, the weight of a person represents the weight of a whole body of the person including the internal body fat and has been used as a typical measure for determining a level of obesity of the person. The weight has been easily measured for many years with a weight scale. Thus, if there is a device capable of measuring the weight used as a measure for determining obesity or the like in relation to health maintenance and providing information on the visceral fat through a simple procedure, a person can individually make a judgment more appropriate for his health maintenance.

It is, therefore, an object of the present invention to provide a visceral fat determining device with a weight-measuring function capable of measuring the weight and providing information on the visceral fat and which can be used at home or the like through a simple procedure.

DISCLOSURE OF THE INVENTION

In order to achieve the object, according to the present invention, a visceral fat determining device with a weight-measuring function comprises:

a weight-measuring means for measuring the weight of a subject when the subject stands on a measuring surface;

an input means for inputting personal data including an abdominal girth $W_L$, which is a circumferential length of a torso of a subject;

a data processing unit that stores the personal data and calculates quantitative information on abdominal visceral fat of the subject based on the personal data; and a display portion that displays the personal data and a result of the calculation performed by the data processing unit, wherein the quantitative information on the abdominal visceral fat of the subject is calculated based on the abdominal girth $W_L$ of the subject.

The state of abdominal visceral fat of the subject has been believed to be strongly correlated with the abdominal girth $W_L$ that is one of physical characteristics of the subject. In the visceral fat determining device with the weight measuring function of the present invention, the weight of the subject can be obtained, and the quantitative information on the abdominal visceral fat of the subject can also be obtained based on the abdominal girth $W_L$ of the subject.

Therefore, the visceral fat determining device with the weight measuring function of the present invention is capable of measuring the weight serving as a measure for determining obesity, which is related to the subject's health condition and providing information on the abdominal visceral fat, which is deeply related to the subject's health condition at home or the like through a simple procedure.

Furthermore, the visceral fat determining device with a weight-measuring function can be configured so that the height of the subject can be inputted as the personal data through the input means, BMI can be calculated based on the height and the weight through the data processing unit, and the quantitative information on the abdominal visceral fat and/or the BMI can be classified into a plurality of ranking levels and displayed accordingly on the display portion.

In this way, the quantitative information on the abdominal visceral fat and/or BMI can be stepwisely judged in accordance with each of the above classified ranking levels.

Furthermore, the visceral fat determining device with a weight-measuring function of the present invention can be configured so that an amount of the abdominal visceral fat can be determined based on the abdominal girth $W_L$ as the quantitative information on the abdominal visceral fat. The amount of the abdominal visceral fat is information deeply related to the subject's health condition and therefore can be determined to foresee a possibility of suffering from adult diseases.

Furthermore, the visceral fat determining device with a weight measuring function further comprises:

Body-fat ratio measuring means for measuring a human body impedance Z of the subject through electrodes in contact with the subject's foot serving as the terminals of the body and for calculating the body-fat ratio FAT of the subject based on the measured body impedance Z and the inputted personal data or part of the data, wherein the body-fat ratio FAT obtained by the body-fat ratio measuring means can be displayed on the display portion.

With this configuration, the visceral fat determining device with a weight-measuring function of the present invention is not only capable of providing the information on the abdominal visceral fat but also capable of providing the body-fat ratio FAT.

Furthermore, according to the present invention, the visceral fat determining device with a weight-measuring function can be configured to calculate an estimated value of an abdominal visceral fat cross-sectional area VA as information related to the visceral fat. When obtaining the estimated value of an abdominal visceral fat cross-sectional area VA, a specific correlation between the abdominal girth $W_L$ and the abdominal visceral fat cross-sectional area VA is determined based on statistical analysis of correlation between actual values of an abdominal visceral fat cross-sectional area VA and the personal data including the abdominal girth $W_L$ of human bodies of random samples. Then, by applying the above-determined correlation to an individual subject, the estimated value of an abdominal visceral fat cross-sectional area VA of the individual subject is believed to be accurately calculated based on the abdominal girth $W_L$ and other data of the individual subject.

A visceral fat determining device with a weight measuring function capable of providing such an estimated value of an abdominal visceral fat cross-sectional area VA comprises:

weight-measuring means for measuring the weight of a subject when the subject stands on a measuring surface;

input means for inputting personal data including an abdominal girth $W_L$, which is a circumferential length of a torso of the subject;

a data processing unit that stores the personal data and calculates an estimated value of an abdominal visceral fat cross-sectional area VA of the subject based on the personal data; and a display portion that displays the personal data and a result of the calculation performed by the data processing unit, wherein the data processing unit stores a first regression coefficient of the abdominal girth $W_L$ and a first regression constant which are obtained based on statistical analysis of correlation between actually measured values of the abdominal visceral fat cross-sectional area VA obtained in abdominal tomography of human bodies of random samples and values of the abdominal girth $W_L$ of the human samples, and the estimated value of an abdominal visceral fat cross-sectional area VA of the subject is obtained based on a value of the abdominal girth $W_L$ of the subject, the first regression coefficient of the abdominal girth $W_L$, and the first regression constant.

The present invention of the visceral fat determining device with a weight-measuring function is based on the fact that the abdominal visceral fat cross-sectional area VA is deeply correlated with the abdominal girth $W_L$. The data processing unit stores a first regression coefficient of the abdominal girth $W_L$ and a first regression constant obtained based on statistical analysis of correlation between actually measured values of the abdominal visceral fat cross-sectional area VA obtained in abdominal tomography of human bodies of random samples and values of the abdominal girths $W_L$ of the human samples. And, when a value of the abdominal girth $W_L$ is inputted, an estimated value of the abdominal visceral fat cross-sectional area VA is calculated based on the first regression coefficient of the abdominal girth $W_L$ and the first regression constant.

As described above, according to the visceral fat determining device with a weight-measuring function of the present invention, the estimated value of an abdominal visceral fat cross-sectional area VA of a subject, which is information related to the visceral fat of the subject that can be easily obtained by inputting a value of the abdominal girth $W_L$, which is part of the personal data. In this way, the estimated value of an abdominal visceral fat cross-sectional area VA, which is information deeply related to the health condition, can be obtained through a simple procedure.

Furthermore, a visceral fat determining device with a weight-measuring function capable of providing an estimated value of an abdominal visceral fat cross-sectional area VA comprises:

weight-measuring means for measuring weight of a subject when the subject stands on a measuring surface;

input means for inputting personal data including an abdominal girth $W_L$ that is a circumferential length of a torso of the subject and the height of the subject;

a data processing unit that stores the personal data and calculates an estimated value of an abdominal visceral fat cross-sectional area VA of the subject based on the personal data; and a display portion that displays the personal data and a result of the calculation performed by the data processing unit, wherein the data processing unit stores a second regression coefficient of the abdominal girth $W_L$, a first regression coefficient of BMI, and a second regression constant which are obtained based on statistical analysis of a correlation between actually measured values of the abdominal visceral fat cross-sectional area VA obtained in abdominal tomography of human bodies of random samples and values of the abdominal girth $W_L$ of the human samples and values of the BMI of the human samples related to the level of the obesity, and the data processing unit calculates the estimated value of an abdominal visceral fat cross-sectional area VA of the subject based on a value of the abdominal girth $W_L$, a value of the BMI, the second regression coefficient of the abdominal girth $W_L$, the first regression coefficient of the BMI, and the second regression constant.

The present invention of the visceral fat determining device with a weight-measuring function is based on the fact that the abdominal visceral fat cross-sectional area VA is correlated with the BMI in addition to the abdominal girth $W_L$. The data processing unit stores a second regression coefficient of the abdominal girth $W_L$ and a first regression coefficient of the BMI, and a second regression constant which are obtained based on a statistical analysis of correlation between actually measured values of the abdominal visceral fat cross-sectional area VA obtained in abdominal tomography of human bodies of random samples and values of the abdominal girth $W_L$ and values of the BMI of the human samples. Then, in the visceral fat determining device with a weight-measuring function of the present invention, when a value of the abdominal girth $W_L$ and a value of the BMI of the subject are inputted, an estimated value of the abdominal visceral fat cross-sectional area VA of the subject is obtained. Therefore, in the visceral fat determining device with a weight-measuring function of the present invention, in addition to the abdominal girth $W_L$, the BMI of the subject can be well reflected in obtaining the abdominal visceral fat cross-sectional area VA.

Furthermore, a visceral fat determining device with a weight-measuring function comprises:

weight-measuring means for measuring weight of a subject when the subject stands on a measuring surface;

input means for inputting personal data including an abdominal girth $W_L$ that is a circumferential length of a torso of the subject, and the height, sex, and age of the subject;

a data processing unit that stores the personal data and calculates an estimated value of an abdominal visceral fat cross-sectional area VA of the subject based on the personal data;

a display portion that displays the personal data and a result of the calculation performed by the data processing unit; and body fat ratio measuring means for measuring a human body impedance Z of the subject through electrodes in contact with terminals of the subject's body and for obtaining a body fat ratio FAT of the subject based on the measured body impedance Z and the inputted personal data or part of the data, wherein the data processing unit stores a third regression coefficient of the abdominal girth $W_L$, a first regression coefficient of the body fat ratio FAT, and a third regression constant which are obtained based on statistical analysis of correlation between actually measured values of the abdominal visceral fat cross-sectional area VA obtained in abdominal tomography of human bodies of random samples and values of the abdominal girth $W_L$ and values of the body fat ratio FAT of the human samples, and the data processing unit calculates the estimated value of an abdominal visceral fat cross-sectional area VA of the subject based on a value of the abdominal girth $W_L$, a value of the body-fat ratio FAT obtained by the body fat-ratio measuring means, the third regression coefficient of the abdominal girth $W_L$, and the first regression coefficient of the body fat-ratio FAT, and the third regression constant.

The invention of the visceral fat determining device with a weight measuring function is based on the fact that the abdominal visceral fat cross-sectional area VA is correlated with the body fat ratio FAT in addition to the abdominal girth $W_L$. The data processing unit stores a third regression coefficient of the abdominal girth $W_L$ and a first regression coefficient of the body fat ratio FAT, and a third regression constant which are obtained based on statistical analysis of a correlation between actually measured values of the abdominal visceral fat cross-sectional area VA obtained in abdominal tomography of human bodies of random samples and values of the abdominal girth $W_L$ and values of the body fat ratio FAT. In the visceral fat determining device with a weight-measuring function, when a value of the abdominal girth $W_L$ and a value of the body fat ratio FAT of the subject are inputted, an estimated value of the abdominal visceral fat cross-sectional area VA of the subject is obtained. Therefore, according to the visceral fat determining device of the present invention, the body-fat ratio FAT of the subject can well be reflected in obtaining the abdominal visceral fat cross-sectional area VA in addition to the abdominal girth $W_L$.

Furthermore, a visceral fat determining device with a weight-measuring function comprises:

weight-measuring means for measuring weight of a subject when the subject stands on a measuring surface;

input means for inputting personal data including an abdominal girth $W_L$ that is a circumferential length of a torso of the subject, height, and a thickness of abdominal subcutaneous fat s of the subject;

a data processing unit that stores the personal data and calculates an estimated value of an abdominal visceral fat cross-sectional area VA of the subject based on the personal data; and a display portion that displays the personal data and a result of the calculation performed by the data processing unit, wherein the data processing unit stores a fourth regression coefficient of the abdominal girth $W_L$, a second regression coefficient of BMI, a first regression coefficient of the thickness of the abdominal subcutaneous fat s, and a fourth regression constant which are obtained based on statistical analysis of correlation between actually measured values of the abdominal visceral fat cross-sectional area VA obtained in abdominal tomography of human bodies of random samples and values of the BMI which is related to the level of obesity of the human samples and values of the thickness of the abdominal subcutaneous fat s of the human samples, and the data processing unit calculates the estimated value of an abdominal visceral fat cross-sectional area VA of the subject based on a value of the abdominal girth $W_L$, a value of the BMI, a value of the thickness of abdominal subcutaneous fat s, the fourth regression coefficient of the abdominal girth $W_L$, the second regression coefficient of the BMI, the first regression coefficient of the thickness of abdominal subcutaneous fat s, and the fourth regression constant.

The present invention of the visceral fat determining device with a weight-measuring function is based on the fact that the abdominal visceral fat cross-sectional area VA is correlated with the BMI and the thickness of the abdominal subcutaneous fat s in addition to the abdominal girth $W_L$. The visceral fat determining device with a weight measuring function of the present invention stores a fourth regression coefficient of the abdominal girth $W_L$, a second regression coefficient of the BMI, a first regression coefficient of the thickness of abdominal subcutaneous fat s, and a fourth regression constant which are obtained based on statistical analysis of correlation between actually measured values of the abdominal visceral fat cross-sectional areas VA obtained in abdominal tomography of human bodies of random samples and values of the abdominal girth $W_L$, values of the BMI, and values of the thickness of abdominal subcutaneous fat s of the human samples. In the visceral fat determining device with a weight-measuring function, when a value of the abdominal girth $W_L$, a value of the BMI, and a value of the thickness of abdominal subcutaneous fat s of the subject are inputted, an estimated value of the abdominal visceral fat cross-sectional area VA of the subject is obtained.

Therefore, in the visceral fat determining device with a weight-measuring function, in addition to the abdominal girth $W_L$, the BMI and the thickness of abdominal subcutaneous fat s can be well reflected in obtaining the abdominal visceral fat cross-sectional area VA.

Furthermore, a visceral fat determining device with a weight-measuring function of the present invention comprises:

weight-measuring means for measuring weight of a subject when the subject stands on a measuring surface;

input means for inputting personal data including an abdominal girth $W_L$ that is a circumferential length of a torso of the subject, height, sex, age, and a thickness of abdominal subcutaneous fat s of the subject;

a data processing unit that stores the personal data and calculates an estimated value of an abdominal visceral fat cross-sectional area VA of the subject based on the personal data;

a display portion that displays the personal data and a result of the calculation performed by the data processing unit; and body fat ratio measuring means for measuring a human body impedance Z of the subject through electrodes in contact with terminals of the subject's body and for obtaining the body fat ratio FAT of the subject based on the measured body impedance Z and the inputted personal data or part of the data, wherein the data processing unit stores a fifth regression coefficient of the abdominal girth $W_L$, a second regression coefficient of the body fat ratio FAT, a second regression coefficient of the thickness of the abdominal subcutaneous fat s and a fifth regression constant which are obtained based on statistical analysis of a correlation between actually measured values of the abdominal visceral fat cross-sectional area VA obtained in abdominal tomography of human bodies of random samples and values of the abdominal girth $W_L$ of the human samples, values of the body-fat ratio FAT of the human samples, and values of the thickness of abdominal subcutaneous fat s, and the data processing unit calculates the estimated value of an abdominal visceral fat cross-sectional area VA of the subject based on a value of the abdominal girth $W_L$, a value of the body-fat ratio FAT obtained with the body-fat ratio measuring means, a value of the thickness of abdominal subcutaneous fat s, the fifth regression coefficient of the abdominal girth $W_L$, the second regression coefficient of the body fat ratio FAT, the second regression coefficient of the thickness of abdominal subcutaneous fat s, and the fifth regression constant.

The present invention of the visceral fat determining device with a weight-measuring function is based on the fact that the abdominal visceral fat cross-sectional area VA is correlated with the body fat-ratio FAT and the thickness of the abdominal subcutaneous fat s in addition to the abdominal girth $W_L$. The visceral fat determining device with a weight-measuring function of the present invention stores a fifth regression coefficient of the abdominal girth $W_L$, a second regression coefficient of the body-fat ratio FAT, a second regression coefficient of the thickness of abdominal subcutaneous fat s, and a fifth regression constant which are obtained based on statistical analysis of correlation between actually measured values of the abdominal visceral fat cross-sectional area VA obtained in abdominal tomography of human bodies of random samples and values of the abdominal girth $W_L$, values of the body-fat ratio FAT, and values of the thickness of abdominal subcutaneous fat s. With this configuration, when a value of the abdominal girth $W_L$, a value of the body-fat ratio FAT, and a value of the thickness of abdominal subcutaneous fat s of the subject are inputted, an estimated value of the abdominal visceral fat cross-sectional area VA of the subject is calculated.

Therefore, in the visceral fat determining device with a weight-measuring function, in addition to the abdominal girth $W_L$, the body-fat ratio FAT and the thickness of the abdominal subcutaneous fat s can be well reflected in obtaining the estimated value of the abdominal visceral fat cross-sectional area VA.

Furthermore, the visceral fat determining device with a weight-measuring function in which the thickness of the abdominal subcutaneous fat s can be inputted can be configured to obtain an abdominal subcutaneous fat cross-sectional area SA based on the thickness of the abdominal subcutaneous fat s and the abdominal girth $W_L$.

Still furthermore, the visceral fat determining device with a weight-measuring function can also be configured to obtain a ratio of the estimated value of an abdominal visceral fat cross-sectional area VA to the abdominal subcutaneous fat cross-sectional area SA of the subject, VSR.

Even furthermore, the visceral fat determining device with a weight-measuring function of the present invention can be configured to obtain a total abdominal fat cross-sectional area WA based on the estimated value of an abdominal visceral fat cross-sectional area VA and the abdominal subcutaneous fat cross-sectional area SA of the subject.

The visceral fat determining device with a weight-measuring function capable of obtaining the abdominal subcutaneous fat cross-sectional area SA offers the following advantages.

Specifically, it has been recently reported that a hormone secreted from the subcutaneous fat of a person tends to reduce internal body fat of the person. Moreover, the subcutaneous fat tends to reduce the negative influence of the visceral fat accumulated in the body due to the intake of excess nutrition. Therefore, information on the abdominal subcutaneous fat or the ratio of the subcutaneous fat to the visceral fat can be used as an important index for assessing the health condition.

Furthermore, a visceral fat determining device with a weight-measuring function of the present invention comprises:

weight-measuring means for measuring weight of a subject when the subject stands on a measuring surface;

input means for inputting personal data including an abdominal girth $W_L$ that is a circumferential length of a torso of the subject and height of the subject;

a data processing unit that stores the personal data and calculates an estimated value of an abdominal visceral fat cross-sectional area VA of the subject based on the personal data; and a display portion that displays the personal data and a result of the calculation performed by the data processing unit, wherein the data processing unit stores a first regression coefficient of a first abdominal girth index and a sixth regression constant which are obtained based on statistical analysis of correlation between actually measured values of the abdominal visceral fat cross-sectional area VA obtained in abdominal tomography of human bodies of random samples and values of the first abdominal girth index of the human samples obtained by dividing a square of the abdominal girth $W_L$ by the height of the human samples and the data processing unit calculates the estimated value of an abdominal visceral fat cross-sectional area VA of the subject based on a value of the first abdominal girth index, the first regression coefficient of the first abdominal girth index, and the sixth regression constant.

In the visceral fat determining device with a weight-measuring function, an estimated value of an abdominal visceral fat cross-sectional area VA of a subject is calculated based on correlation with the first abdominal girth index. Herein, an abdominal girth index is defined as an index obtained by dividing a value of a square of the abdominal girth $W_L$ of a subject's body by height of the subject. This index is believed to be deeply correlated with obesity of the subject.

Furthermore, a visceral fat determining device with a weight-measuring function of the present invention comprises:

weight-measuring means for measuring weight of a subject when the subject stands on a measuring surface;

input means for inputting personal data including an abdominal girth $W_L$ that is a circumferential length of a torso of the subject, and a height, sex, and age of the subject;

a data processing unit that stores the personal data and calculates an estimated value of an abdominal visceral fat cross-sectional area VA of the subject based on the personal data;

a display portion that displays the personal data and a result of the calculation performed by the data processing unit; and body-fat ratio measuring means for measuring a human body impedance Z of the subject through electrodes in contact with feet of the subject as terminals of the subject's body and for calculating a body-fat ratio FAT of the subject based on the measured body impedance Z and the inputted personal data or part of the data, wherein the data processing unit stores a sixth regression coefficient of the abdominal girth $W_L$, a third regression coefficient of BMI, a third regression coefficient of the body-fat ratio FAT, and a ninth regression constant which are obtained based on statistical analysis of a correlation between actually measured values of the abdominal visceral fat cross-sectional area VA obtained in abdominal tomography of human bodies of random samples and values of the BMI of the human samples and values of the body fat ratio FAT of the human samples and the estimated value of the abdominal visceral fat cross-sectional area VA of the subject is obtained based on a value of the abdominal girth $W_L$, a value of the BMI, a value of the body-fat ratio FAT, the sixth regression coefficient of the abdominal girth $W_L$, the third regression coefficient of the BMI, the third regression coefficient of the body-fat ratio FAT, and the ninth regression constant.

The present invention of the visceral fat determining device with a weight-measuring function is based on the fact that the abdominal visceral fat cross-sectional area VA is correlated with the BMI and the body-fat ratio FAT in addition to the abdominal girth $W_L$. The visceral fat determining device with a weight-measuring function of the present invention stores a sixth regression coefficient of the abdominal girth $W_L$, a third regression coefficient of the BMI, a third regression coefficient of the body fat ratio FAT, and a ninth regression constant which are obtained based on statistical analysis of correlation between actually measured values of the abdominal visceral fat cross-sectional area VA obtained in abdominal tomography of human bodies of random samples and values of the abdominal girth $W_L$ of the human samples, values of the BMI of the human samples, and values of the body-fat ratio FAT of the human samples. In the visceral fat determining device with a weight measuring function, by inputting values of the abdominal girth $W_L$ of the BMI, and of the body-fat ratio FAT of the subject, an estimated value of the abdominal visceral fat cross-sectional area VA of the subject can be obtained.

Therefore, in the visceral fat determining device with a weight-measuring function, in addition to the abdominal girth $W_L$, the BMI and the body-fat ratio FAT can be well reflected in obtaining the estimated value of the abdominal visceral fat cross-sectional area VA.

Furthermore, a visceral fat determining device with a weight-measuring function comprises:

weight-measuring means for measuring weight of a subject when the subject stands on a measuring surface;

input means for inputting personal data including an abdominal girth $W_L$ that is a circumferential length of a torso of the subject, and a height, sex, age, and a thickness of abdominal subcutaneous fat s of the subject;

a data processing unit that stores the personal data and calculates an estimated value of an abdominal visceral fat cross-sectional area VA of the subject based on the personal data; and a display portion that displays the personal data and a result of the calculation performed by the data processing unit, and body-fat ratio measuring means for measuring a human body impedance Z of the subject through electrodes in contact with feet of the subject as terminals of the subject's body and for calculating a body-fat ratio FAT of the subject based on the measured body impedance and the inputted personal data or part of the data, wherein the data processing unit stores a seventh regression coefficient of the abdominal girth $W_L$, a fourth regression coefficient of BMI, a fourth regression coefficient of the body fat ratio FAT, a third regression coefficient of the thickness of abdominal subcutaneous fat s, and a tenth regression constant, which are obtained based on statistical analysis of a correlation between actually measured values of the abdominal visceral fat cross-sectional area VA obtained in abdominal tomography of human bodies of random samples and values of the BMI of the human samples, values of the body-fat ratio FAT of the human samples, and values of the thickness of the abdominal subcutaneous fat s of the human samples and the estimated value of the abdominal visceral fat cross-sectional area VA of the subject is obtained based on a value of the abdominal girth $W_L$, a value of the BMI, a value of the body-fat ratio FAT, a value of the thickness of abdominal subcutaneous fat s, the seventh regression coefficient of the abdominal girth $W_L$, the fourth regression coefficient of the BMI, the fourth regression coefficient of the body fat ratio FAT, the third regression coefficient of the thickness of abdominal subcutaneous fat s, and the tenth regression constant.

The present invention of the visceral fat determining device with a weight-measuring function is based on the fact that the abdominal visceral fat cross-sectional area VA is correlated with the BMI, the body fat ratio FAT, and the thickness of abdominal subcutaneous fat s in addition to the abdominal girth $W_L$. The visceral fat determining device with a weight-measuring function stores a seventh regression coefficient of the abdominal girth $W_L$, a fourth regression coefficient of the BMI, a fourth regression coefficient of the body-fat ratio FAT, a third regression coefficient of the thickness of the abdominal subcutaneous fat s, and a tenth regression constant which are obtained based on statistical analysis of a correlation between actually measured values of the abdominal visceral fat cross-sectional area VA obtained in abdominal tomography of human bodies of random samples and values of the abdominal girth $W_L$ of the human samples, values of the BMI of the human samples, values of the body-fat ratio FAT of the human samples, and values of the thickness of the abdominal subcutaneous fat s of the human samples.

In the visceral fat determining device with a weight-measuring function, by inputting a value of the abdominal girth $W_L$, a value of the BMI, a value of the body fat ratio FAT, and a value of the thickness of abdominal subcutaneous fat s of the subject, an estimated value of the abdominal visceral fat cross-sectional area VA of the subject can be obtained. Therefore, in the visceral fat determining device with a weight measuring function, in addition to the abdominal girth $W_L$, the BMI, the body-fat ratio FAT, and the thickness of abdominal subcutaneous fat s can be well reflected in obtaining the estimated value of the abdominal visceral fat cross-sectional area VA.

Furthermore, a visceral fat determining device with a weight measuring function of the present invention comprises:

weight-measuring means for measuring a weight of a subject when the subject stands on a measuring surface;

input means for inputting personal data including an abdominal girth $W_L$ that is a circumferential length of a torso of the subject and height of the subject;

a data processing unit that stores the personal data and calculates an estimated value of an abdominal visceral fat cross-sectional area VA of the subject based on the personal data; and a display portion that displays the personal data and a result of the calculation performed by the data processing unit, and an impedance-measuring means for measuring a human body impedance Z of the subject through electrodes in contact with terminals of the subject's body, wherein the data processing unit stores an eighth regression coefficient of the abdominal girth WL, a first regression coefficient of a term (TL2/Z), and an eleventh regression constant which are obtained based on statistical analysis of correlation between the actually measured values of the abdominal visceral fat cross-sectional area VA obtained in abdominal tomography of human bodies of random samples and values of the abdominal girth WL of the human samples and values of the term (TL2/Z) obtained by dividing a square of height TL by the body impedance Z and the data processing unit calculates the estimated value of an abdominal visceral fat cross-sectional area VA of the subject based on a value of the abdominal girth $W_L$, a value of the body impedance Z measured with the impedance-measuring means, a value of the height $T_L$ obtained through the input means, the eighth regression coefficient of the abdominal girth $W_L$, and the first regression coefficient of the term $(T_L^2/Z)$, and the eleventh regression constant.

The present invention of the visceral fat determining device with a weight-measuring function is based on the fact that the abdominal visceral fat cross-sectional area VA is correlated with the term $(T_L^2/Z)$ in addition to the abdominal girth $W_L$. The visceral fat determining device with a weight-measuring function stores an eighth regression coefficient of the abdominal girth $W_L$, and a first regression coefficient of the term $(T_L^2/Z)$ and an eleventh regression constant obtained based on statistical analysis of a correlation between actually measured values of the abdominal visceral fat cross-sectional areas VA obtained in abdominal tomography of human bodies of random samples and values of the abdominal girth $W_L$ and values of the term $(T_L^2/Z)$.

In the visceral fat determining device with a weight-measuring function, when a value of the abdominal girth $W_L$ and a value of the height $T_L$ of the subject are inputted together with a value of the measured body impedance Z, an estimated value of the abdominal visceral fat cross-sectional area VA of the subject can be obtained. Therefore, in the visceral fat determining device of the present invention, in addition to the abdominal girth $W_L$, the term $(T_L^2/Z)$ can be reflected in obtaining the estimated value of the abdominal visceral fat cross-sectional area VA.

Furthermore, a visceral fat determining device with a weight-measuring function of the present invention comprises:

weight-measuring means for measuring a weight of a subject when the subject stands on a measuring surface;

input means for inputting personal data including an abdominal girth $W_L$ that is a circumferential length of a torso of the subject and height of the subject;

a data processing unit that stores the personal data and calculates an estimated value of an abdominal visceral fat-cross sectional area VA of the subject based on the personal data;

a display portion that displays the personal data and a result of the calculation performed by the data processing unit; and impedance-measuring means for measuring a human body impedance Z of the subject through electrodes in contact with terminals of the subject's body, wherein the data processing unit stores a ninth regression coefficient of the abdominal girth $W_L$, a first regression coefficient of the body impedance Z, and a twelfth regression constant which are obtained based on statistical analysis of a correlation between actually measured values of the abdominal visceral fat cross-sectional area VA obtained in abdominal tomography of human bodies of random samples and values of the abdominal girth $W_L$ of the human samples and values of the body impedance Z of the human samples and the data processing unit calculates the estimated value of an abdominal visceral fat cross-sectional area VA of the subject based on a value of the abdominal girth $W_L$, a value of the body impedance Z measured with the impedance measuring means, the ninth regression coefficient of the abdominal girth $W_L$, and the first regression coefficient of the body impedance Z, and the twelfth regression constant.

The present invention of the visceral fat determining device is based on the fact that the abdominal visceral fat cross-sectional area VA is correlated with the human body impedance Z in addition to the abdominal girth $W_L$. The visceral fat determining device stores a ninth regression coefficient of the abdominal girth $W_L$, a first regression coefficient of the body impedance Z, and a twelfth regression constant which are obtained based on statistical analysis of correlation between actually measured values of an abdominal visceral fat cross-sectional area VA obtained in abdominal tomography of human bodies of random samples and values of the abdominal girth $W_L$ of the human samples and values of the body impedance Z of the human samples.

In the visceral fat determining device with a weight measuring function, by inputting a value of the abdominal girth $W_L$ of the subject and measuring the body impedance Z, an estimated value of the abdominal visceral fat cross-sectional area VA of the subject can be obtained. Therefore, in the visceral fat determining device with a weight-measuring function, in addition to the abdominal girth $W_L$, the body impedance Z can be reflected in obtaining the estimated value of the abdominal visceral fat cross-sectional area VA.

Furthermore, a visceral fat determining device with a weight-measuring function of the present invention comprises:

weight-measuring means for measuring weight of a subject when the subject stands on a measuring surface;

input means for inputting personal data, including an abdominal girth $W_L$ that is a circumferential length of a torso of a subject, and a height, sex, and age of the subject;

a data processing unit that stores the personal data and calculates an estimated value of an abdominal visceral fat cross-sectional area VA of the subject based on the personal data;

a display portion that displays the personal data and a result of the calculation performed by the data processing unit; and body-fat ratio measuring means for measuring a human body impedance Z of the subject through electrodes in contact with terminals of the subject's body and for obtaining a body fat ratio FAT of the subject based on the measured body impedance Z and the inputted personal data or part of the data, wherein the data processing unit stores a first regression coefficient of a term ($W_L^2 \cdot T_L \cdot age$) and a first regression coefficient of a term ($W_L^2 \cdot T_L \cdot FAT$), and a thirteenth regression constant which are obtained based on statistical analysis of a correlation between actually measured values of the abdominal visceral fat cross-sectional area VA obtained in abdominal tomography of human bodies of random male samples and values of the term ($W_L^2 \cdot T_L \cdot age$) obtained by multiplying a square of an abdominal girth $W_L$ of the human samples, the height $T_L$ of the human samples, and the age of the human samples and values of the term of ($W_L^2 \cdot T_L \cdot FAT$) obtained by multiplying a square of the abdominal girth $W_L$ of the human samples, the height $T_L$ of the human samples, and the body-fat ratio FAT of the human samples and when inputted subject's personal data of sex is "male" through the input means, the data processing unit calculates the estimated value of the abdominal visceral fat cross-sectional area VA of the male subject based on a value of the abdominal girth $W_L$ of the male subject, a value of the age of the male subject inputted through the input means, a value of the body-fat ratio FAT of the male subject measured with the body-fat ratio measuring means, the first regression coefficient of the term ($W_L^2 \cdot T_L \cdot age$), the first regression coefficient of the term ($W_L^2 \cdot T_L \cdot FAT$), and the thirteenth regression constant.

In the case that the subject is male, the present invention of the visceral fat determining device with a weight-measuring function is based on the fact that the abdominal visceral fat cross-sectional area VA is deeply correlated with the terms ($W_L^2 \cdot T_L \cdot age$) and ($W_L^2 \cdot T_L \cdot FAT$) representing the physical characteristics. Therefore, the visceral fat determining device with a weight measuring function stores a first regression coefficient of the term ($W_L^2 \cdot T_L \cdot age$), a first regression coefficient of the term ($W_L^2 \cdot T_L \cdot FAT$), and a thirteenth regression constant which are obtained based on statistical analysis of correlation between actually measured values of the abdominal visceral fat cross-sectional area VA obtained in abdominal tomography of human bodies of random male samples and values of the term ($W_L^2 \cdot T_L \cdot age$) of the human male samples and values of the term ($W_L^2 \cdot T_L \cdot FAT$) of the human male samples.

By inputting a value of the abdominal girth $W_L$ and a value of the height $T_L$ of the male subject and by measuring the body-fat ratio FAT of the male subject, an estimated value of the abdominal visceral fat cross-sectional area VA of the male subject can be obtained. In the case that the subject is male, in the visceral fat determining device with a weight-measuring function, an estimated value of the abdominal visceral fat cross-sectional area VA of the male subject is more accurately obtained.

Furthermore, a visceral fat determining device with a weight-measuring function of the present invention comprises:

weight-measuring means for measuring weight of a subject when the subject stands on a measuring surface;

input means for inputting personal data including an abdominal girth $W_L$ that is a circumferential length of a torso of the subject, and a height, weight, sex, and age of the subject;

a data processing unit that stores the personal data and calculates an estimated value of an abdominal visceral fat cross-sectional area VA of the subject based on the personal data;

a display portion that displays the personal data and a result of the calculation performed by the data processing unit; and body-fat ratio measuring means for measuring a human body impedance Z of the subject through electrodes in contact with terminals of the subject's body and for obtaining a body-fat ratio FAT of the subject based on the measured body impedance Z and the inputted personal data or part of the data, wherein the data processing unit stores a second regression coefficient of the term ($W_L^2 \cdot T_L \cdot age$), a fifth regression coefficient of the body fat ratio FAT, and a fourteenth regression constant which are obtained based on statistical analysis of a correlation between actually measured values of the abdominal visceral fat cross-sectional area VA obtained in abdominal tomography of human bodies of random female samples and values of the term ($W_L^2 \cdot T_L \cdot age$) obtained by multiplying a square of the abdominal girth $W_L^2$ of the human samples, the height $T_L$ of the human samples, and the age of the human samples and values of the body fat ratio FAT of the human samples and in the case that inputted subject's personal data of sex is "female," the data processing unit calculates the estimated value of the abdominal visceral fat cross-sectional area VA of the female subject based on a value of the abdominal girth $W_L$ of the female subject, a value of the age of the female subject inputted through the input means, a value of the body fat ratio FAT of the female subject measured with the body fat ratio measuring means, the second regression coefficient of the term ($W_L^2 \cdot T_L \cdot age$), the fifth regression coefficient of the term body fat ratio FAT, and the fourteenth regression constant.

The present invention of the visceral fat determining device with a weight-measuring function is based on the fact that the abdominal visceral fat cross-sectional area VA is deeply correlated with the term ($W_L^2 \cdot T_L \cdot age$) and the body-fat ratio FAT of the female subject. The visceral fat determining device stores a second regression coefficient of the term ($W_L^2 \cdot T_L \cdot age$) and a fifth regression coefficient of the body-fat ratio FAT, and a fourteenth regression constant which are obtained based on statistical analysis of correlation between actually measured values of the abdominal visceral fat cross-sectional area VA obtained in abdominal tomography of human bodies of random female samples and values of the term ($W_L^2 \cdot T_L \cdot age$) of the human female samples and values of the body fat ratio FAT of the human female samples.

By inputting a value of the abdominal girth $W_L$, a value of the height $T_L$, and a value of the age of the female subject and by measuring the body-fat ratio FAT, an estimated value of the abdominal visceral fat cross-sectional area VA of the female subject can be obtained. As described above, in the visceral fat determining device with a weight-measuring function, in the case that the subject is female, an estimated value of the abdominal visceral fat cross-sectional area VA is more accurately obtained.

Furthermore, the visceral fat determining device with a weight-measuring function can be configured such that the estimated value of an abdominal visceral fat cross-sectional area VA of the subject can be obtained with addition of a correction term of the age and a correction term of the sex of the subject.

In this way, the physical characteristics of the subject such as age and sex can be well reflected in obtaining the estimated value of the abdominal visceral fat cross-sectional area VA of the subject. In this case, the estimated value of an abdominal visceral fat cross-sectional area VA of the subject can be corrected with the age or the sex, or both of them.

Furthermore, the visceral fat determining device with a weight-measuring function capable of providing an estimated value of the abdominal visceral fat cross-sectional area VA can be configured such that a plurality of ranking levels are defined in advance, based on a plurality of standard values for the abdominal visceral fat cross-sectional area VA, and the estimated value of the abdominal visceral fat cross-sectional area VA is displayed on the display portion in accordance with a plurality of the ranking levels.

In this way, since the measured result given as the quantitative information of the abdominal visceral fat cross-sectional area VA can be visually grasped through a visually graded scale on the display, understanding of the obtained abdominal visceral fat cross-sectional area VA becomes easier.

Furthermore, the visceral fat determining device with a weight-measuring function capable of calculating the estimated value of the abdominal visceral fat cross-sectional area VA based on correlation with the BMI can be configured such that a plurality of ranking levels are in advance defined based on a plurality of standard values for the BMI, and the BMI of the subject is displayed on the display portion in accordance with the ranking levels.

Furthermore, the visceral fat determining device with a weight-measuring function can be configured so that, in addition to a plurality of ranking levels of the BMI to be defined in advance, based on a plurality of standard values for the BMI, a plurality of ranking levels are defined in advance based on a plurality of standard values for the abdominal visceral fat cross-sectional area VA and, in addition to the BMI of the subject, the obtained estimated value of the abdominal visceral fat cross-sectional area VA of the subject is also displayed on the display portion in accordance with the ranking levels.

Furthermore, the visceral fat determining device with a weight-measuring function capable of obtaining the estimated value of the abdominal visceral fat cross-sectional area VA based on correlation with the BMI can be configured such that a judging standard value is in advance defined for each of the abdominal girth $W_L$, the BMI, and the abdominal visceral fat cross-sectional area VA, and obesity of a subject is judged based on comparison of each of values of the abdominal girth $W_L$, the BMI, and the abdominal visceral fat cross-sectional area VA of the subject with each of the judging standard values defined in advance.

Furthermore, the judging standard values to be defined in advance can be set to be 25 for the BMI, 100 cm$^2$ for the abdominal visceral fat cross-sectional area VA, 85 cm for the abdominal girth $W_L$ of male subjects, and 90 cm for the abdominal girth $W_L$ of female subjects.

Furthermore, the visceral fat determining device with a weight-measuring function can be configured such that measured results of the weight and the abdominal visceral fat cross-sectional area VA are stored for a certain length of time, and amounts of changes between the stored weight which is a measured result in the past and the weight measured most recently and between the stored abdominal visceral fat cross-sectional area VA which is a measured result in the past and the abdominal visceral fat cross-sectional area VA measured most recently can be obtained.

Moreover, the visceral fat determining device with a weight-measuring function can also be configure such that a ratio of the amount of the change of the abdominal visceral fat cross-sectional area VA to the amount of the change of the weight (the amount of the change of the abdominal visceral fat cross-sectional area VA/the amount of change of the weight) can be obtained.

Furthermore, a circumferential length of an abdomen at 4$^{th}$ lumbar vertebrae of the subject can be used as the abdominal girth $W_L$. In this way, use of the abdominal girth $W_L$ obtained at the portion of the subject enables the measurer to obtain measured results strongly correlated with the visceral fat condition of the subject.

BRIEF DESCRIPTION OF THE DRAWINGS

FIG. 1(*b*) is a view representing an example of a display of the visceral fat determining device with a weight-measuring function;

FIG. 5 is a table representing a set of judging standard values for obesity.

BEST MODE FOR CARRYING OUT THE INVENTION

Figure 1:
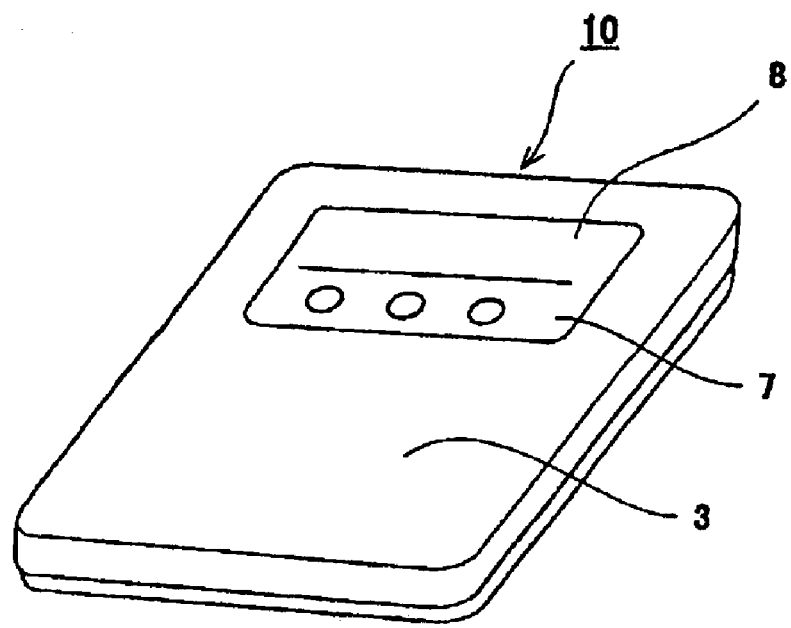
FIG. 1(*a*) is a perspective view of an example of a visceral fat determining device with a weight-measuring function.
Figure 1:
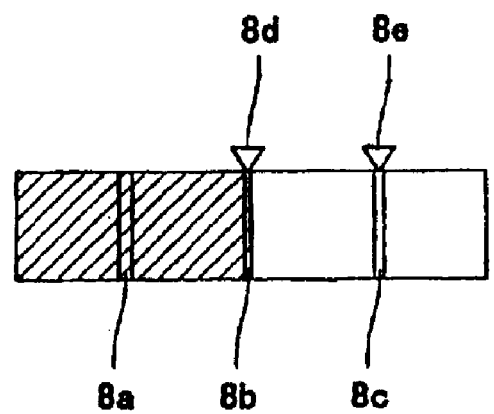

A preferred embodiment of the present invention will be described referring to FIGS. 1–5. FIG. 1 shows a visceral fat determining device with a weight-measuring function 10 (hereinafter, referred to as "visceral fat determining device 10") as an example of a preferred embodiment of the present invention. FIG. 1(*a*) is a perspective view of the visceral fat determining device 10.

The visceral fat determining device 10 comprising weight-measuring means for measuring the weight of a subject when a subject stands on a measuring surface 3. Specifically, the weight of the subject is measured in such a way that a load cell (not shown) provided inside the visceral fat determining device 10 detects the weight, and then the detected result is digitized.

Furthermore, the visceral fat determining device 10 is capable of obtaining information related to the visceral fat of the subject such as an estimated value of an abdominal visceral fat cross-sectional area VA, which is a cross-sectional area of the visceral fat at the abdomen and a total abdominal fat cross-sectional area WA including abdominal subcutaneous fat.

Furthermore, with the visceral fat determining device 10, BMI, which has been conventionally used as an index of obesity level, can be also obtained. The BMI is to be obtained through a well known formula developed based on the subject's height and weight as part of the personal data as described later.

The visceral fat determining device 10 is provided with an operation portion 7 including a plurality of keys to be used for inputting numerical values, letters, and so on. Through these keys, the personal data representing physical characteristics of the subject can be inputted. In other words, a plurality of keys necessary for inputting the personal data are provided. That is, the operation portion 7 corresponds to serve as means for inputting the personal data.

The personal data to be inputted into the visceral fat determining device 10 include height and waist size (hereinafter, referred to as "abdominal girth") of the subject. As the abdominal girth $W_L$, a circumferential length of an abdomen at the 4$^{th}$ lumbar vertebra of the subject is preferred because it is strongly correlated with the state of the visceral fat of the subject.

Furthermore, the personal data to be inputted may also include a thickness of abdominal subcutaneous fat s of the subject, which can be measured using a number of well known subcutaneous fat thickness measuring means such as a caliper, an ultrasonic probe, and so on.

Moreover, the thickness of abdominal subcutaneous fat s of the subject to be inputted into the visceral fat determining device may be the value at the side umbilical region, the value at the upper part of the ilium, the sum thereof, or an average of the sum.

Furthermore, in calculating the abdominal visceral fat cross-sectional area VA, as described later, if formula requiring data of an human body impedance Z and a body-fat ratio FAT of the subject is to be used, values of the body impedance Z and the body-fat ratio FAT of the subject can be inputted through an operation portion 7. In other words, known values of the body impedance Z and the body-fat ratio FAT of the subject obtained elsewhere can be inputted through the use of the operation portion 7.

The operation portion 7 is provided with a plurality of keys such as a selection key for selecting items of the personal data and numeric keys for inputting values. Furthermore, the operation portion 7 is also provided with an ON/OFF power switch for turning on and off the visceral fat determining device 10 and an impedance measurement starting switch for starting a measurement of a bioelectrical impedance Z to be explained later. Furthermore, with the operation portion 7, a plurality of measurement modes can be selected for the abdominal visceral fat cross-sectional area VA. In accordance with the selected mode, a corresponding measurement routine such as a first measurement routine and a second measurement routine that will be described later is executed.

A display portion 8 displays various kinds of the personal data inputted through the operation portion 7, a measured value of the weight, and a value of the BMI calculated from the inputted personal data and the weight value, as well as information associated with the abdominal visceral fat cross-sectional area VA.

FIG. 1(b) is a view of an example of the display on the display portion 8. In FIG. 1(b), a measured result of the abdominal visceral fat cross-sectional area VA is shown as classified in a plurality of ranking levels. Those indicated by 8a, 8b, and 8c in FIG. 1(b) are ranking bars representing the ranking levels. A plurality of standard values are defined in advance for the BMI and the abdominal visceral fat cross-sectional area VA, and then compared with measured values of the BMI and the abdominal visceral fat cross-sectional area VA. And, then, which ranking levels the measured values of the BMI and the abdominal visceral fat cross-sectional area VA of the subject are classified to is determined and displayed. According to the example given in FIG. 1(b), the display shows that the value of the abdominal visceral fat cross-sectional area VA of the subject corresponds to the ranking bar 8b.

Furthermore, as shown in FIG. 1(b), level indicators 8d and 8e can also be displayed. The level indicators 8d and 8e can be correlated with specific symptoms related to the visceral fat. For example, if a value of the abdominal visceral fat cross-sectional area VA of a person is larger than 100 cm$^2$, or a value of the BMI of the person is higher than 25, then, the person may be clinically diagnosed to be obese. Therefore, the level indicator 8e may be set to correspond to 100 cm$^2$ for the abdominal visceral fat cross-sectional area VA or to 25 for the BMI.

As shown in FIG. (b), displaying a measured result obtained as a quantitative value in accordance with ranking levels or displaying the measured result in accordance with symptoms of possible diseases from which the person might be suffering can allow visual, stepwise, and lucid interpretation of the results in accordance with the measured result.

Figure 2:
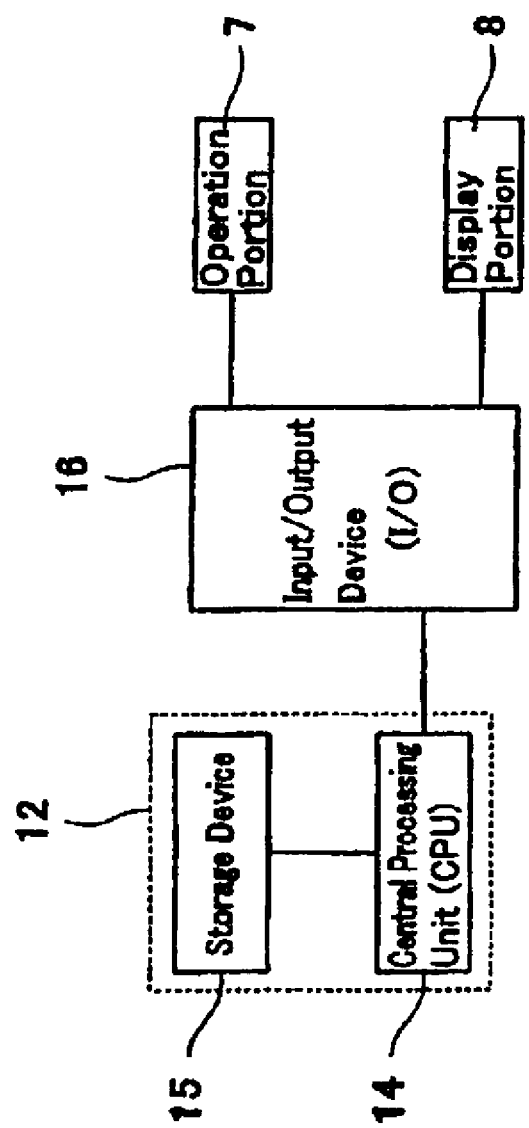
FIG. 2 is a schematic block diagram representing a signal processing in the visceral fat determining device with a weight-measuring function.

Referring to FIG. 2, a block diagram representing signal processing in the visceral fat determining device 10 is described. Various types of calculations can be performed by a data processing unit 12 including a central processing unit (CPU) 14 and a storage device 15.

The storage device 15 stores the personal data inputted through the function keys provided with the operation portion 7. The storage device 15 also stores weight data measured through the weight measuring means. Furthermore, once estimated values of the BMI and the abdominal visceral fat cross-sectional area VA are obtained, they are also stored in the storage device 15.

Furthermore, the storage device 15 stores an operation instruction routine including procedures necessary for giving the subject required guidance and instructions on how to operate the visceral fat determining device 10 and measurement routines including procedures for calculating BMI, the body-fat ratio FAT, and the estimated values of the abdominal visceral fat cross-sectional area VA. The measurement routines include a first measurement routine and a second measurement routine as described later in an execution example of the measurement routines.

Furthermore, the storage device 15 stores a first regression coefficient $a_1$ of the abdominal girth $W_L$, a second regression coefficient $a_2$ of the abdominal girth $W_L$, a third regression coefficient $a_3$ of the abdominal girth $W_L$, a fourth regression coefficient $a_4$ of the abdominal girth $W_L$, a fifth regression coefficient $a_5$ of the abdominal girth $W_L$, a sixth regression coefficient $a_6$ of the abdominal girth $W_L$, a seventh regression coefficient $a_7$ of the abdominal girth $W_L$, a eighth regression coefficient $a_8$ of the abdominal girth $W_L$, a ninth regression coefficient $a_9$ of the abdominal girth $W_L$, a first regression coefficient $f_1$ of the first abdominal girth index, a second regression coefficient $f_2$ of the second abdominal girth index, a first regression coefficient $b_1$ of BMI, a second regression coefficient $b_2$ of BMI, a third regression coefficient $b_3$ of BMI, a fourth regression coefficient $b_4$ of BMI, a first regression coefficient $d_1$ of the body fat ratio FAT, a second regression coefficient $d_2$ of the body-fat ratio FAT, a third regression coefficient $d_3$ of the body-fat ratio FAT, a fourth regression coefficient $d_4$ of the body-fat ratio FAT, a fifth regression coefficient $d_5$ of the body-fat ratio FAT, a first regression coefficient $e_1$ of the thickness of abdominal subcutaneous fat s, a second regression coefficient $e_2$ of the thickness of abdominal subcutaneous fat s, a third regression coefficient $e_3$ of the thickness of abdominal subcutaneous fat s, a first regression constant $c_1$, a second regression constant $c_2$, a third regression constant $c_3$, a fourth regression constant $c_4$, a fifth regression constant $c_5$, a sixth regression constant $c_6$, an eighth regression constant $c_8$, an eleventh regression constant $c_{11}$, a twelfth regression constant $c_{12}$, a thirteenth regression constant $c_{13}$, and a fourteenth regression constant $c_{14}$.

Furthermore, the storage device 15 stores a first regression coefficient $h_1$ for the term $(W_L^2 \cdot T_L \cdot FAT)$ obtained by multiplying a square of the abdominal girth $W_L^2$, the height $T_L$, and the body-fat ratio FAT and a first regression coefficient $i_1$ for the term $(W_L^2 \cdot T_L \cdot age)$ obtained by multiplying a square of the abdominal girth $W_L^2$, the height $T_L$, and the age.

Furthermore, the storage device 15 stores a second regression coefficient $i_2$ for the term $(W_L^2 \cdot T_L \cdot age)$ obtained by multiplying a square of the abdominal girth $W_L^2$, the height $T_L$, and the age.

These regression coefficients and constants $a_1$, $a_2$, $a_3$, $a_4$, $a_5$, $a_6$, $a_7$, $a_8$, $a_9$, $b_1$, $b_2$, $b_3$, $b_4$, $c_1$, $c_2$, $c_3$, $c_4$, $c_5$, $c_6$, $c_8$, $c_9$, $c_{10}$, $c_{11}$, $c_{12}$, $c_{13}$, $c_{14}$, $d_1$, $d_2$, $d_3$, $d_4$, $d_5$, $e_1$, $e_2$, $e_3$, $f_1$, $f_2$, $g_1$, $h_1$, $i_1$, $i_2$, and $j_1$ are obtained elsewhere and then inputted into the visceral fat determining device 10 for storage.

These regression coefficients and constants are obtained in the following procedure. Specifically, the actual abdominal visceral fat cross-sectional area VA of each of a number of individuals who are randomly selected is measured. In addition, the abdominal girth $W_L$, the BMI, the impedance Z, the body-fat ratio FAT, the thickness of abdominal subcutaneous fat s, and the height $T_L$ of each of the individuals are also measured.

The first regression coefficient $a_1$, of the abdominal girth $W_L$ and the first regression constant $c_1$ can be obtained by statistically correlating the abdominal girth $W_L$ with the actually measured abdominal visceral fat cross-sectional area VA. Also, the second regression coefficient $a_2$ of the abdominal girth $W_L$, the first regression coefficient $b_1$, of the BMI, and the second regression constant $c_2$ can be obtained by statistically analyzing correlation between the abdominal girth $W_L$, the BMI, and the actually measured abdominal visceral fat cross-sectional area VA.

Moreover, the third regression coefficient $a_3$ of the abdominal girth $W_L$, the first regression coefficient $d_1$ of the body-fat ratio FAT, and the third regression constant $c_3$ can be obtained by statistically analyzing correlation between the abdominal girth $W_L$, the body-fat ratio FAT, and the actually measured abdominal visceral fat cross-sectional area VA.

Furthermore, the fourth regression coefficient $a_4$ of the abdominal girth $W_L$, the second regression coefficient $b_2$ of the BMI, the first regression coefficient $e_1$ of the thickness of abdominal subcutaneous fat s, and the fourth regression constant $c_4$ can be obtained by statistically analyzing correlation between the abdominal girth $W_L$, the BMI, the thickness of abdominal subcutaneous fat s and the actually measured abdominal visceral fat cross-sectional area VA.

What is more, the fifth regression coefficient $a_5$ of the abdominal girth $W_L$, the second regression coefficient $d_2$ of the body-fat ratio FAT, the second regression coefficient $e_2$ of the thickness of abdominal subcutaneous fat s, and the fifth regression constant $c_5$ can be obtained by statistically analyzing correlation between the abdominal girth $W_L$, the body-fat ratio FAT, the thickness of abdominal subcutaneous fat s, and the actually measured abdominal visceral fat cross-sectional area VA.

Furthermore, the sixth regression coefficient $a_6$ of the abdominal girth $W_L$, the third regression coefficient $b_3$ of the BMI, the third regression coefficient $d_3$ of the body-fat ratio FAT, and the ninth regression constant $c_9$ can be obtained by statistically analyzing correlation among the abdominal girth $W_L$, the BMI, the body-fat ratio FAT, and the actually measured abdominal visceral fat cross-sectional area VA.

Furthermore, the seventh regression coefficient $a_7$ of the abdominal girth $W_L$, the fourth regression coefficient $b_4$ of the BMI, the fourth regression coefficient $d_4$ of the body-fat ratio FAT, and the tenth regression constant $c_{10}$ can be obtained by statistically analyzing correlation among the abdominal girth $W_L$, the BMI, the body-fat ratio FAT, the thickness of abdominal subcutaneous fat s, and the actually measured abdominal visceral fat cross-sectional area VA.

Even furthermore, the first regression coefficient $f_1$ of the first abdominal girth index, and the sixth regression constant $c_6$ can be obtained by statistically correlating the first abdominal girth index obtained by dividing a square of the abdominal girth $W_L$ by the height with the actually measured abdominal visceral fat cross-sectional area VA. Also, the second regression coefficient $f_2$ of the second abdominal girth index, and the eighth regression constant $c_8$ can be obtained by statistically correlating the second abdominal girth index obtained by dividing a square of the abdominal girth $W_L$ by the height with the actually measured abdominal visceral fat cross-sectional area VA.

Furthermore, the eighth regression coefficient $a_8$ of the abdominal girth $W_L$, the first regression coefficient $j_1$ for the term $(T_L^2/Z)$, and the eleventh regression constant $c_{11}$ can be obtained by statistically analyzing correlation among the abdominal girth $W_L$, the term $(T_L^2/Z)$, and the actually measured abdominal visceral fat cross-sectional area VA.

Also, the ninth regression coefficient $a_9$ of the abdominal girth $W_L$, the first regression coefficient $g_1$ for the impedance Z, and the twelfth regression constant $c_{12}$ can be obtained by statistically analyzing correlation among the abdominal girth $W_L$, the impedance Z, and the actually measured abdominal visceral fat cross-sectional area VA.

Also, the first regression coefficient $i_1$ for the term $(W_L^2 \cdot T_L \cdot age)$, the first regression coefficient $h_1$ for the term $(W_L^2 \cdot T_L \cdot FAT)$, and the thirteenth regression constant $c_{13}$ can be obtained by statistically analyzing correlation among the term $(W_L^2 \cdot T_L \cdot age)$, the term $(W_L^2 \cdot T_L \cdot FAT)$, and the actually measured abdominal visceral fat cross-sectional area VA.

Specifically, the first regression coefficient $i_1$ for the term $(W_L^2 \cdot T_L \cdot age)$, the first regression coefficient $h_1$ for the term $(W_L^2 \cdot T_L \cdot FAT)$, and the thirteenth regression constant $c_{13}$ are statistically determined based on human bodies of a number of male subjects who are randomly selected. More specifically, these coefficients $i_1$, $h_1$, and $c_{13}$ are, as described later, used in formula to calculate an estimated value of an abdominal visceral fat cross-sectional area VA of a subject in the case that the subject is male.

The second regression coefficient $i_2$ for the term $(W_L^2 \cdot T_L \cdot age)$, the fifth regression coefficient $d_5$ of the body fat ratio FAT, and the fourteenth regression constant $c_{14}$ can be obtained by statistically analyzing correlation between the term $(W_L^2 \cdot T_L \cdot age)$, the body-fat ratio FAT, and the abdominal visceral fat cross-sectional area VA.

Specifically, the second regression coefficient $i_2$ for the term $(W_L^2 \cdot T_L \cdot age)$, the fifth regression coefficient $d_5$ of the body-fat ratio FAT, and the fourteenth regression constant $c_{14}$ are statistically determined based on human bodies of a number of female subjects who are randomly selected. More specifically, these coefficient $i_2$, $d_5$, and $c_{14}$ are, as described later, used in formula to calculate an estimated value of an abdominal visceral fat cross-sectional area VA of a subject in the case that the subject is female.

In order to determine these coefficients from $a_1$, to $j_1$, the actually measured abdominal visceral fat cross-sectional area VA can be statistically correlated with personal data of each individual subject by means of a regression analysis. For example, the first regression coefficient $a_1$ of the abdominal girth $W_L$ and the first regression constant $c_1$ obtained with respect to $a_1$ can be obtained by single regression analysis based on an assumption that the actually measured abdominal visceral fat cross-sectional area VA is exclusively correlated with the abdominal girth $W_L$. Furthermore, when there is a correlation between the abdominal girth $W_L$, other personal data, and actually measured abdominal visceral fat cross-sectional area VA, then the coefficients can be obtained by multiple regression analysis.

The abdominal visceral fat cross-sectional area VA of human bodies of random samples is actually obtained through tomography. This tomography can be provided with a plurality of different means such as CT scanning, MRI, ultrasonic diagnosis, and any other methods capable of performing accurate measurements of human abdominal cross-sections. Furthermore, in determining the coefficients from $a_1$ to $j_1$, the number of subjects required for statistically analyzing the abdominal visceral fat cross-sectional area VA should preferably be more than 100, more preferably more than 500.

Referring to a block diagram representing signal processing in the visceral fat determining device 10 in FIG. 2, data and measured values stored in the storage device 15 can be displayed on the display portion 8. Furthermore, the data and measured values are inputted/outputted to/from the central processing unit 14 and the storage device 15 through an input/output device 16 for further processing.

Figure 3:
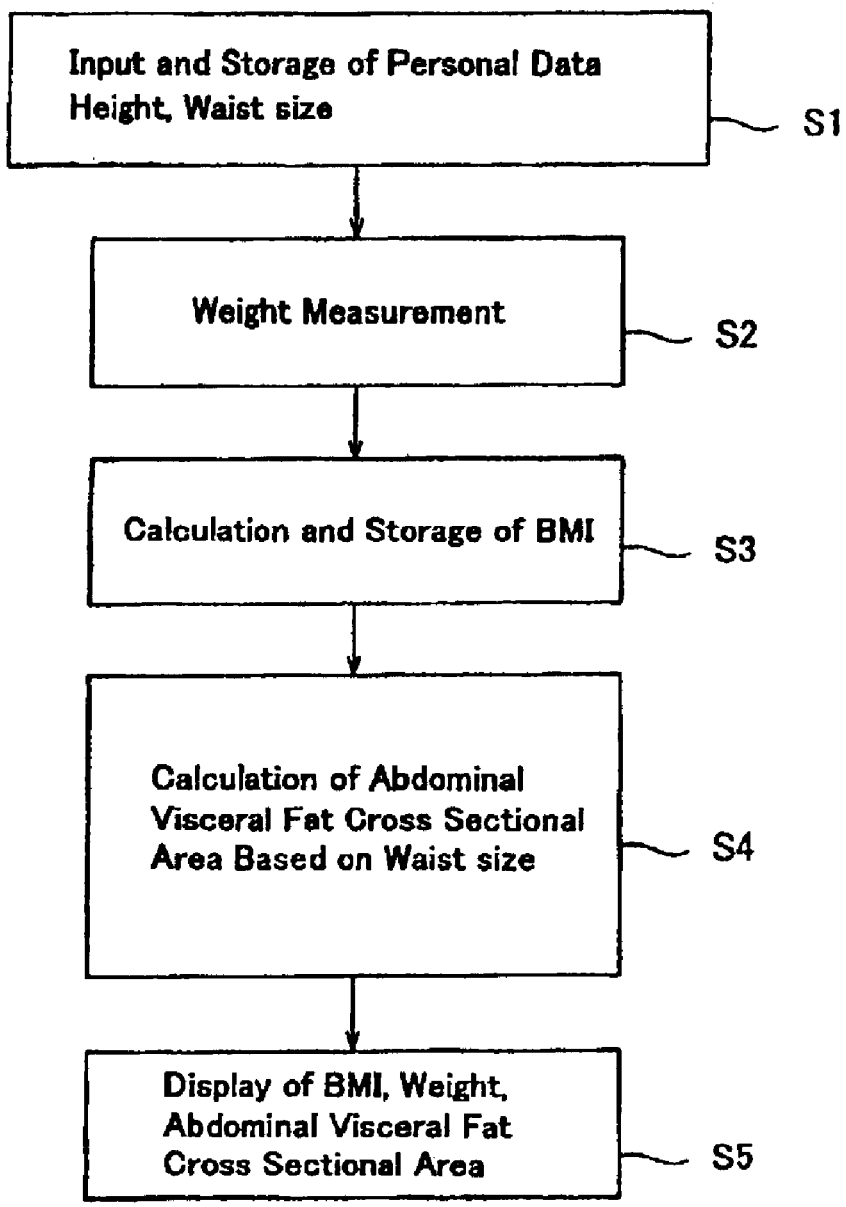
FIG. 3 is a flow chart representing an example of procedures required to measure an abdominal visceral fat cross-sectional area.

Referring to FIG. 3, an example of the operation of the visceral fat determining device 10 will be described. When the visceral fat determining device 10 is turned on, and the first measurement mode is selected through the operation portion 7, the first measurement routine is started.

First, personal data which are body specific information including height, weight, age, sex, and abdominal girth $W_L$ of a subject are inputted by the subject and stored (S1).

Then, the subject stands on the weight measuring surface and the weight is measured and stored (S2). A value of the BMI is obtained through the calculation based on the height inputted in (S1) and the weight measured in (S2) and stored (S3). An estimated value of the abdominal visceral fat cross-sectional area VA is calculated from the abdominal girth $W_L$ (S5). The value of the BMI, the value of the weight, and the estimated value of the abdominal visceral fat cross-sectional area VA obtained above are displayed on the display portion 8 (S5).

In procedure (S5), when the obtained results are displayed on the display portion 8, more than one of the values of the BMI, the weight, and the abdominal visceral fat cross-sectional area VA may be displayed simultaneously. In the case in which more than of the obtained results are displayed, if the values of the weight and the abdominal visceral fat cross-sectional area VA are simultaneously displayed, the relationship between the two are understood directly from what is displayed on the display portion 8.

The estimated value of the abdominal visceral fat cross-sectional area VA in (S5) is calculated with formula (1).

$$VA = a_1 \cdot W_L + c_1 \quad (1)$$

In procedure (S5) shown in FIG. 3, the abdominal visceral fat cross-sectional area VA is assumed to exclusively correlate with the abdominal girth $W_L$ of the subject, and the estimated value of VA is calculated using the coefficients of a1 and c1 and the abdominal girth $W_L$. The formula (1) may be replaced by the following formulae from (2) to (9) to calculate the estimated value of VA.

$$VA = a_2 \cdot W_L + b_1 \cdot BMI + c_2 \quad (2)$$

$$VA = a_3 \cdot W_L + d_1 \cdot FAT + c_3 \quad (3)$$

$$VA = a_4 \cdot W_L + b_2 \cdot BMI + e_1 \cdot s + c_4 \quad (4)$$

$$VA = a_5 \cdot W_L + d_2 \cdot FAT + e_2 \cdot s + c_5 \quad (5)$$

$$VA = a_6 \cdot W_L + b_3 \cdot BMI + d_3 \cdot FAT + c_9 \quad (6)$$

$$VA = a_7 \cdot W_L + b_4 \cdot BMI + d_4 \cdot FAT + e_3 \cdot s + c_{10} \quad (7)$$

$$VA = a_8 \cdot W_L + j_1 \cdot (T_L^2/2) + c_{11} \quad (8)$$

$$VA = a_9 \cdot W_L + g_1 \cdot Z + c_{12} \quad (9)$$

In formula (2), the estimated value of VA is calculated based on the assumption that the VA is exclusively correlated with the abdominal girth $W_L$ and BMI of the subject.

In formula (3), the VA is calculated based on the assumption that the VA is exclusively correlated with the abdominal girth $W_L$ and the body-fat ratio FAT of the subject.

In formula (4), the estimated value of VA is calculated based on the assumption that the VA is exclusively correlated with the abdominal girth $W_L$, BMI, and thickness of abdominal subcutaneous fat s of the subject.

In formula (5), the estimated value of VA is calculated based on the assumption that the VA is exclusively correlated with the abdominal girth $W_L$, the body-fat ratio FAT, and the thickness of abdominal subcutaneous fat s of the subject.

In formula (8), the estimated value of VA is calculated based on the assumption that the VA is exclusively correlated with the abdominal girth $W_L$ and the term $(T_L^2/Z)$ obtained by dividing the square of the height $T_L^2$ by the impedance Z of the subject.

In formula (9), the estimated value of VA is calculated based on the assumption that the VA is exclusively correlated with the abdominal girth $W_L$ and the impedance Z of the subject.

As should be understood from the above, while, in the formula (1), the estimated value of VA is calculated based on the correlation with the abdominal girth $W_L$, in the formulae from (2) to (9), the estimated value of VA is calculated based on the correlation with a plurality of terms of the personal data. Therefore, the formulae from (2) to (9), with the correlation of a plurality of values of the personal data, can provide the estimated value of VA with more precise reflection of the physical characteristics of the individual subject.

In formula (4), (5), or (7) including the thickness of abdominal subcutaneous fat s, the estimated value of VA can reflect the thickness of abdominal subcutaneous fat of the subject.

On the other hand, the calculation of an estimated value of VA using the formula (1)–(3), (6), (8), (9) has the following advantage. Measurement of a thickness of the abdominal subcutaneous fat s require burdensome procedure such as measuring with a caliper or the like. With the formulae (1)–(3), (6), (8), (9), however, a thickness of the abdominal subcutaneous fat s is not required to be inputted. Thus, in obtaining an estimated value of VA using the formulae (1)–(3), (6), (8), (9), the burdensome procedure of obtaining the thickness of the abdominal subcutaneous fat s can be avoided.

The estimated value of VA can be calculated based on assumption that the VA is exclusively correlated with the abdominal girth index. In formulae (10) and (11), the estimated value of VA can be calculated based on correlation with the abdominal girth index.

$$VA = f_1 \cdot (W_L^2/T_L) + c_6 \qquad (10)$$

$$VA = f_2 \cdot (W_L/T_L) + c_8 \qquad (11)$$

In formula (10), the estimated value of VA can be calculated based on correlation with the first abdominal girth index. In formula (11), the estimated value of VA can be calculated based on correlation with the second abdominal girth index. In formulae (10) and (11), $T_L$ is height of the subject.

The first abdominal girth index in formula (10) can be obtained by the term $(W_L^2/T_L)$. The second abdominal girth index in formula (11) can be obtained by the term $(W_L/T_L)$ With formula (10) or (11), the estimated value of VA can be calculated based on correlation with the first abdominal girth index or the second abdominal girth index which is known to be highly correlated with obesity.

Furthermore, the estimated value of VA can be calculated based on correlation with the terms $(W_L^2 \cdot T_L \cdot age)$ and $(W_L^2 \cdot T_L \cdot FAT)$. In formula (12), the estimated value of VA can be calculated based on correlation with the terms $(W_L^2 \cdot T_L \cdot age)$ and $(W_L^2 \cdot T_L \cdot FAT)$.

$$VA = i_1 \cdot W_L^2 \cdot T_L \cdot age + h_1 \cdot W_L^2 \cdot T_L \cdot FAT - c_{13} \qquad (12)$$

With the formula (12), the estimated value of VA can be more accurately calculated when the subject is male. Therefore, in the case where "male" is entered as the sex of the subject through the operation portion 7, the formula (12) should be chosen to accurately calculate the estimated value of VA for the male subject.

Also, the estimated value of VA can be calculated based on correlation with the term $(W_L^2 \cdot T_L \cdot age)$ and the body-fat ratio FAT. In formula (13), the estimated value of VA can be calculated based on correlation with the term $(W_L^2 \cdot T_L \cdot age)$ and body-fat ratio FAT.

$$VA = i_2 \cdot W_L^2 \cdot T_L \cdot age + d_5 \cdot FAT - c_{14} \qquad (13)$$

With the formula (13), the estimated value of VA can be more accurately calculated when a subject is a female. Therefore, in the case where "female" is entered as the sex of the subject through the operation portion 7, the formula (13) should be chosen to accurately calculate the estimated value of VA for the female subject.

Furthermore, each of the formulae from (1) to (13) may include correction terms on the basis of age and sex. The age correction term Yc is given by formula (14), and the sex correction term Xc is given by formula (15).

$$Yc = -\delta \cdot age \qquad (14)$$

$$Xc = \eta \cdot sex \qquad (15)$$

In formula (14), "age" is the age of the subject, and $\delta$ is an age correction coefficient. Also, in formula (15), "sex" is a variable depending on the sex of the subject, and $\eta$ is a sex correction coefficient. In the case that these correction terms are included in the formulae from (1) to (13), they are defined and treated as variable terms of the multiple regression equation. Therefore, $\delta$ and age are defined as a regression coefficient and a variable respectively in the formula (14). Also, $\eta$ and sex are defined as a regression coefficient and a variable respectively in the formula (15). These are obtained based on correlation with the estimation formulae for VA.

Addition of the correction terms Xc given by the formula (14) and Yc given by the formula (15) to the formulae from (1) to (13) in the calculation of VA makes it possible to more precisely reflect the personal physical characteristics of the subject in terms of age and sex.

Either one or both of the correction terms Xc and Yc may be added to the formulae from (1) to (13). If both of the terms Xc and Yc are added in the calculation of VA using any one of the formulae from (1) to (13), it becomes possible to obtain the VA with more precise reflection of the personal physical characteristics of the subject.

Furthermore, the visceral fat determining device 10 described above can be provided with body fat ratio measuring means (not shown) for measuring a body fat-ratio FAT of a subject. Specifically, a pair of current path forming electrodes to form an electric current path within the body of the subject and a pair of voltage measurement electrodes to measure a human body impedance of the subject are formed on a measuring surface of the visceral fat determining device 10. These electrodes are provided in such a way that each of the soles of the left and right feet of the subject is in contact with one of the current path forming electrodes and one of the voltage measurement electrodes when the subject stands on the measuring surface 3.

An electric current source being connected with a pair of the current path forming electrodes provides an electric current flowing into the body of the subject and impedance measuring means contacting a pair of the voltage measurement electrodes which measure the potential difference between the electrodes. In this way, a human body impedance Z can be measured through both of the feet as terminals of the body of the subject.

Furthermore, since required personal data are needed in obtaining a body fat-ratio FAT of the subject, the required personal data such as age and sex of the subject may be inputted through the operation portion 7.

And, the above measured body impedance of the subject and the personal data inputted through the operation portion 7 are stored in the storage device 15. Furthermore, various kinds of formulae and coefficients necessary for calculation of the body-fat ratio FAT based on the body impedance Z and the personal data are stored in the storage device 15, and the body-fat ratio FAT is obtained by calculation through the data processing unit 12.

If a human body impedance Z and a body-fat ratio FAT of a subject can be measured in such a way as described above, the measured results of the body impedance Z and body-fat ratio FAT of the subject can be used in obtaining the abdominal visceral fat area VA.

In this way, the abdominal visceral fat area VA of the subject related to information of the visceral fat can be obtained through calculation using latest values of the body impedance Z and body-fat ratio FAT of the subject to be timely measured on-site.

Furthermore, an amount of the abdominal visceral fat of the subject which is given as information related to the visceral fat can also be calculated based on the abdominal visceral fat cross-sectional area VA thus obtained.

Figure 4:
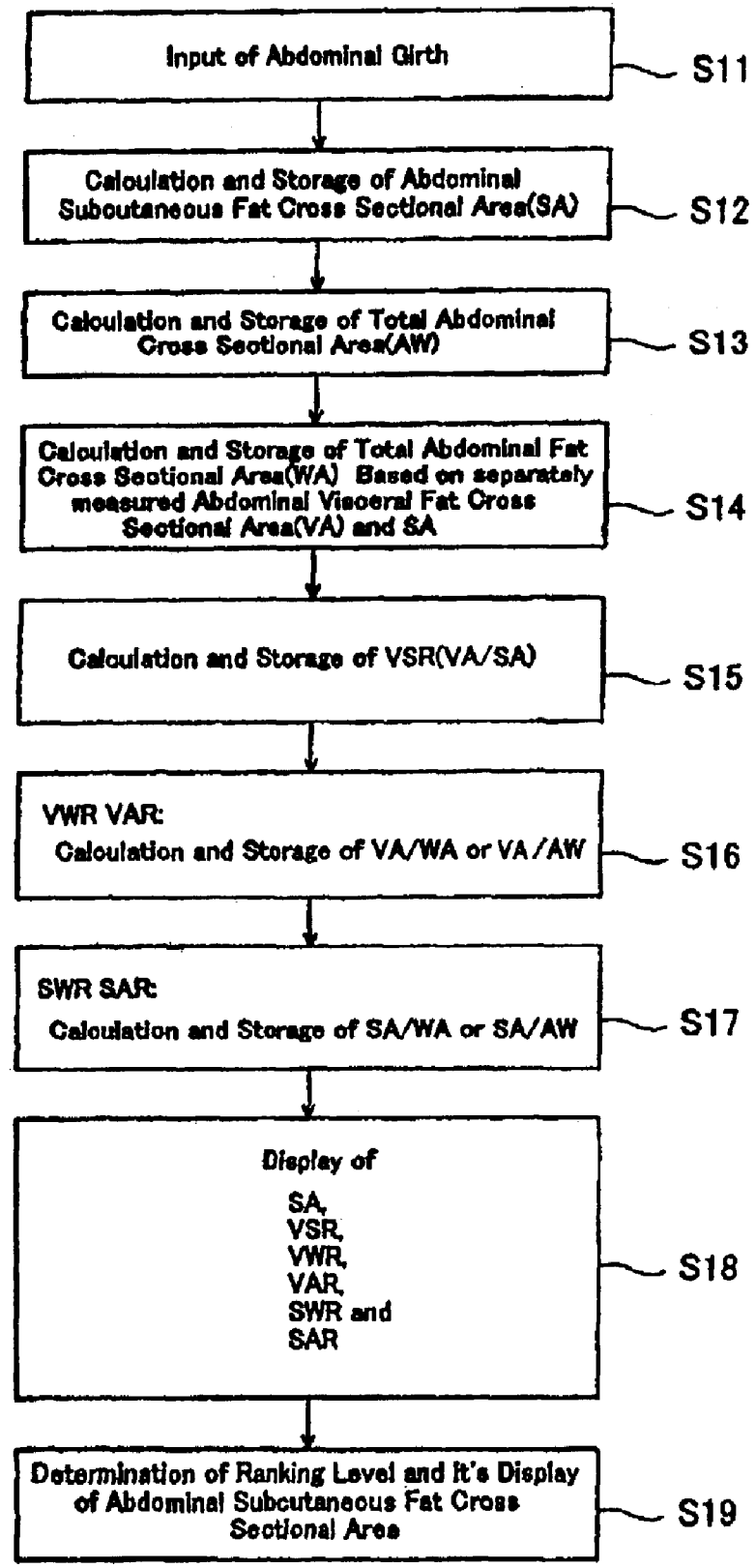
FIG. 4 is a flow chart representing an example of procedures required to measure various kinds of cross-sectional areas at an abdominal portion.

Next, referring to FIG. 4, another operational example of the visceral fat determining device 10 will be described. When the second measurement mode is selected through the operation portion 7, then the second measurement routine is started. First, a circumferential length of a torso of a subject as the abdominal girth $W_L$ is inputted by the subject (S11). Then, the subcutaneous fat cross-sectional area (SA) is calculated and stored (S12). In step (S12), the calculation of the SA is performed by using the following formula (16).

$$SA = W_L \cdot s - \pi \cdot s^2 \qquad (16)$$

In formula (16), $W_L$ is the circumferential length of the abdomen and s is the thickness of the abdominal subcutaneous fat of the subject.

Then, a total abdominal cross-sectional area AW is calculated and stored (S13). In step (S13), AW is calculated by using the following formula (17).

$$AW = \zeta \cdot (W_L^2/4\pi) \quad (17)$$

In formula (17), $\pi$ is the circular constant pi. $\zeta$ is a conversion coefficient for a conversion between circular and oval circumferences.

Then, based on the abdominal visceral fat cross-sectional area VA and SA, the total abdominal fat cross-sectional area WA is calculated and stored (S14). In step (S14), the WA is calculated by using the following formula (18).

$$WA = VA + SA \quad (18)$$

Then, VSR, a ratio of the abdominal visceral fat cross-sectional area VA to the abdominal subcutaneous fat cross sectional area SA, is calculated and stored (S15). In step (S15), VSR is calculated by using the following formula (19).

$$VSR = VA/SA \quad (19)$$

Then, a VWR which is a ratio of the abdominal visceral fat cross-sectional area VA to the total abdominal fat cross-sectional area WA and a VAR which is a ratio of the abdominal visceral fat cross-sectional area VA to the total abdominal fat cross-sectional area AW are calculated and stored (S16). In step (S16), VWR and VAR are calculated by using the following formulae (20) and (21) respectively.

$$VWR = VA/WA \quad (20)$$

$$VAR = VA/AW \quad (21)$$

Then, a SWR, a ratio of the abdominal subcutaneous fat cross sectional area SA to the abdominal total fat cross-sectional area of WA, and a SAR, a ratio of the abdominal subcutaneous fat cross-sectional area SA to the total abdominal cross-sectional area AW, are calculated and stored (S17). In step (S17), SWR and SAR are calculated by using the following formulae (22) and (23) respectively.

$$SWR = SA/WA \quad (22)$$

$$SAR = SA/AW \quad (23)$$

Then, calculated values of SA, VSR, VWR, VAR, SWR, and SAR are displayed on the display portion 8 (S18). Furthermore, the abdominal subcutaneous fat cross-sectional area SA is rated in a plurality of ranking levels and displayed on the display portion 8 in accordance with the ranking (S19).

In the above description referring to FIGS. from 1 to 4, the abdominal girth $W_L$ which is part of the personal data of the subject was described to be measured elsewhere and then inputted in through the operation portion 7. Alternatively, the visceral fat determining device may be provided with size measuring means capable of measuring the abdominal girth of the subject.

For example, a measuring tape may be stored in the visceral fat determining device 10 and pulled upward from the measuring surface 3 to measure the abdominal girth $W_L$.

Furthermore, the visceral fat determining device of the present invention can be configured to obtain amounts of changes between measured results obtained in the past and measured results obtained most recently of the weight and the abdominal visceral fat area VA. Specifically, measured results of the weight and the abdominal visceral fat area VA are stored for a certain length of time, and amounts of changes between these values of the weight and abdominal visceral fat area VA which were obtained in the past and values of the weight and the abdominal visceral fat area VA which were obtained most recently are obtained through calculation.

Furthermore, the visceral fat determining device can be configured to obtain through calculation a ratio of the amount of the change of the abdominal visceral fat cross-sectional area VA to the amount of the change of the weight (the amount of change of the abdominal visceral fat cross-sectional area VA/the amount of change of the weight) based on the amounts of the changes thus obtained for the abdominal visceral fat cross-sectional area VA and the amount of the change of the weight. By obtaining the ratio of the amount of the change of the abdominal visceral fat cross-sectional area VA to the amount of the change of the weight, a rate of the change of the abdominal visceral fat cross-sectional area VA against the change of the weight can be understood. Therefore, based on the rate of the change of the abdominal visceral fat cross-sectional area VA against the change of the weight, health maintenance such as reducing the visceral fat can be adequately managed.

And, in displaying the obtained amounts of the changes on the display portion 8, both the amount of the change of the weight and the amount of the change of the abdominal visceral fat cross-sectional area VA may be simultaneously displayed. If both the amount of the change of the weight and the amount of the change of the abdominal visceral fat cross-sectional area VA are simultaneously displayed, the relationship between both of the amounts of the changes can be grasped directly from what is displayed on the display portion 8.

While, in the preceding example, an amount of change of the weight and an amount of change of the abdominal visceral fat cross-sectional area VA are used in obtaining an amount of change between a measured result in the past and a measured result obtained most recently, an amount of change of the weight and an amount of change of the visceral fat may also be used. Likewise, in obtaining a ratio between the amounts of the changes, a ratio of the amount of the change of the visceral fat to the amount of the change of the weight (the amount of the change of the visceral fat/the amount of the change of the weight) may also be used.

Furthermore, in the visceral fat determining device 10 of the present invention, obesity can be judged in the following way. Judging standard values for judging obesity are in advance inputted and set in the data processing unit 12 and compared with the above obtained values of the abdominal girth, the BMI, and the abdominal visceral fat cross-sectional area VA for the judgement.

FIG. 5 shows a set of judging standard values used to judge obesity. In the standard of judgment shown in FIG. 5, judging standard values of the BMI, of the abdominal girth, and of the abdominal visceral fat cross-sectional area VA are defined for male and female subjects.

Specifically, for the male subjects, the judging standard values are set to be 25 for the BMI, 85 cm for the abdominal girth, and 100 cm² for the abdominal visceral fat cross-sectional area VA. Also, for the female subjects, the judging standard values are set to be 25 for the BMI, 90 cm for the abdominal girth, and 100 cm² for the abdominal visceral fat cross-sectional area VA.

Based on the judging standard values shown in FIG. 5, the following judgments can be made. If a value of the BMI exceeds the judging standard value, it is judged that there is a probability that the subject suffers from obesity. If a value of the abdominal girth exceeds the judging standard value, it is judged that there is a probability that the subject suffers from upper body obesity. If a value of the abdominal visceral fat cross-sectional area VA exceeds the judging standard value, it is judged that there is a probability that the subject suffers from visceral fat obesity.

Furthermore, based on the judging standard values shown in FIG. 5, a judgment can be made through two steps, the first step and the second step. For example, the first step judgment can be based on values of the BMI and the abdominal girth. Furthermore, the second step judgment can be based on a value of the abdominal visceral fat cross-sectional area VA.

And, if both of the values of the BMI and the abdominal girth exceed their standard values, it is judged that there is a probability that the subject suffers from obesity or upper body obesity. If the value of the abdominal visceral fat cross-sectional area VA also exceeds the standard value, then, it is judged that the subject suffers from visceral fat obesity. Moreover, based on the combined results from the first and the second steps together, it is judged that the subject suffers from obesity.

Incidentally, these judged results can be displayed on the display portion 8 so that the subject can confirm the results.

Furthermore, the visceral fat determining device 10 described thus far can be further provided with height-measuring means. With this provision, a value of the height necessary for obtaining the BMI is not required to be inputted in through the operation portion 7, thereby shortening the measurement time.

INDUSTRIAL APPLICABILITY

As has been described thus far, in a visceral fat determining device with a weight-measuring function of the present invention, the weight of a subject serving as a measure for obesity can be measured and an abdominal visceral fat cross-sectional area VA of the subject can be obtained at home or the like through a simple operation. Specifically, since the abdominal visceral fat cross-sectional area VA serving as an index for obesity which is closely associated with adult diseases can be easily measured, use of the abdominal visceral fat cross-sectional area VA, together with a measured result of the weight, will enable to accurately and easily make a comprehensive judgment concerning the possibility that the subject suffers from various kinds of adult diseases.

What is claimed is:

1. A visceral fat determining device with a weight-measuring function comprising:
    weight-measuring means for measuring a weight of a subject when the subject stands on a measuring surface;
    input means for inputting personal data, including an abdominal girth $W_L$, which is a circumferential length of a torso of the subject;
    data processing unit that stores the personal data and calculates quantitative information on abdominal visceral fat of the subject including an estimated value of an abdominal visceral fat cross-sectional area VA of the subject based on the personal data; and
    a display portion that displays the personal data and a result of the calculation performed by the data processing unit;
    wherein the quantitative information on the abdominal visceral fat of the subject includes at least one regression coefficient and a regression constant which are obtained based on statistical analysis of a correlation between actually measured values of the abdominal visceral fat cross-sectional area VA obtained in abdominal tomography of human bodies of random samples and at least values of the abdominal girth $W_L$ of the human samples; and
    wherein the estimated value of an abdominal visceral fat cross-sectional area VA of the subject is obtained based on a value of the abdominal girth $W_L$, the first regression coefficient of the abdominal girth $W_L$, and the first regression constant.

2. The visceral fat determining device with a weight-measuring function according to claim 1, wherein
    a height of the subject as the personal data can be inputted through the input means,
    a Body Mass Index (BMI) can be calculated based on the height and the weight through the data processing unit, and
    the quantitative information on the abdominal visceral fat and/or Body Mass Index (BMI) classified into a plurality of ranking levels can be displayed on the display portion.

3. The visceral fat determining device with a weight-measuring function according to claim 1, wherein the quantitative information on the abdominal visceral fat includes an amount of the abdominal visceral fat.

4. The visceral fat determining device with a weight-measuring function according to claim 1, further comprising:
    body-fat ratio measuring means for measuring a human body impedance Z of the subject through electrodes in contact with feet of the subject as terminals of the subject's body and for calculating a body-fat ratio FAT of the subject based on the measured body impedance and the inputted personal data or part of the data, wherein
    the body-fat ratio FAT obtained by the body-fat ratio measuring means is displayed on the display portion.

5. The visceral fat determining device with a weight-measuring function according to claim 1, wherein the abdominal girth $W_L$ is a circumferential length of an abdomen at a $4^{th}$ lumbar vertebra of the subject.

6. A visceral fat determining device with a weight-measuring function comprising:
    weight-measuring means for measuring a weight of a subject when the subject stands on a measuring surface;
    input means for inputting personal data including an abdominal girth $W_L$ that is a circumferential length of a torso of the subject;
    a data processing unit that stores the personal data and calculates an estimated value of an abdominal visceral fat cross-sectional area VA of the subject based on the personal data; and
    a display portion that displays the personal data and a result of the calculation performed by the data processing unit, wherein
    the data processing unit stores a first regression coefficient of the abdominal girth $W_L$ and a first regression constant which are obtained based on statistical analysis of a correlation between actually measured values of the abdominal visceral fat cross-sectional area VA obtained in abdominal tomography of human bodies of random samples and values of the abdominal girth $W_L$ of the human samples and
    the estimated value of an abdominal visceral fat cross-sectional area VA of the subject is obtained based on a value of the abdominal girth $W_L$, the first regression coefficient of the abdominal girth $W_L$, and the first regression constant.

7. The visceral fat determining device with a weight-measuring function according to claim 6, wherein the calculation of the estimated value of the abdominal visceral fat cross-sectional area VA of the subject is perform with addition of a correction term of the age and/or a correction term of the sex of the subject.

8. The visceral fat determining device with a weight-measuring function according to claim 6, wherein the estimated value of the abdominal visceral fat cross-sectional area VA of the subject is displayed on the display portion in accordance with a plurality of ranking levels which are in advance defined by a plurality of standard values for the abdominal visceral fat cross-sectional area VA.

9. The visceral fat determining device with a weight-measuring function according to claim 6, wherein measured results of the weight and the abdominal visceral fat cross-sectional area VA are stored for a certain length of time and amounts of changes between the stored weight, which is a measured result in the past, and the weight measured most recently, and between the stored abdominal visceral fat cross-sectional area VA, which is a measured result in the past, and the abdominal visceral fat cross-sectional area VA measured most recently can be obtained.

10. The visceral fat determining device with a weight-measuring function according to claim 6, wherein measured results of the weight and the abdominal visceral fat cross-sectional area VA are stored for a certain length of time, amounts of changes between the stored weight, which is a measured result in the past, and the weight measured most recently, and between the stored abdominal visceral fat cross-sectional area VA, which is a measured result in the past, and the abdominal visceral fat cross-sectional area VA measured most recently can be obtained, and a ratio of the amount of the change of the abdominal visceral fat cross-sectional area VA to the amount of the change of the weight (the amount of the change of the abdominal visceral fat cross-sectional area VA/the amount of the change of the weight) can be obtained.

11. A visceral fat determining device with a weight-measuring function comprising:

weight-measuring means for measuring a weight of a subject when the subject stands on a measuring surface;

input means for inputting personal data, including an abdominal girth $W_L$, that is a circumferential length of a torso of the subject and height of the subject;

a data processing unit that stores the personal data and calculates an estimated value of an abdominal visceral fat cross-sectional area VA of the subject based on the personal data; and a display portion that displays the personal data and a result of the calculation performed by the data processing unit, wherein the data processing unit stores a second regression coefficient of the abdominal girth $W_L$, a first regression coefficient of Body Mass Index (BMI), and a second regression constant which are obtained based on statistical analysis of a correlation between actually measured values of the abdominal visceral fat cross-sectional area VA obtained in abdominal tomography of human bodies of random samples and values of the abdominal girth $W_L$ of the human samples and values of the Body Mass Index (BMI) related to a level of obesity of the human samples and the estimated value of the abdominal visceral fat cross-sectional area VA of the subject is obtained based on a value of the abdominal girth $W_L$, a value of the Body Mass Index (BMI), the second regression coefficient of the abdominal girth $W_L$, the first regression coefficient of the Body Mass Index (BMI), and the second regression constant.

12. The visceral fat determining device with a weight-measuring function according to claim 11, wherein a plurality of ranking levels are defined in advance based on a plurality of standard values for the Body Mass Index (BMI), and the Body Mass Index (BMI) of the subject is displayed on the display portion in accordance with the ranking levels.

13. The visceral fat determining device with a weight-measuring function according to claim 11, wherein a plurality of ranking levels are defined in advance based on a plurality of standard values for the Body Mass Index (BMI), a plurality of ranking levels are defined in advance based on a plurality of standard values for the abdominal visceral fat cross-sectional area VA, the Body Mass Index (BMI) of the subject is displayed on the display portion in accordance with the pre-defined ranking levels, and the abdominal visceral fat cross-sectional area VA of the subject is displayed on the display portion in accordance with the pre-defined ranking levels.

14. The visceral fat determining device with a weight-measuring function according to claim 11, wherein a judging standard value is defined in advance for each of the abdominal girth $W_L$, the Body Mass Index (BMI), and the abdominal visceral fat cross-sectional area VA and obesity of the subject is judged based on comparison of each of values of the abdominal girth $W_L$, the Body Mass Index (BMI), and the abdominal visceral fat cross-sectional area VA with each of the pre-defined judging standard values.

15. The visceral fat determining device with a weight-measuring function according to claim 11, wherein a judging standard value for the Body Mass Index (BMI) is defined in advance to be 25, a judging standard value for the abdominal visceral fat cross-sectional area VA is defined in advance to be 100 $cm^2$, a judging standard value for the abdominal girth $W_L$ of male subjects is defined in advance to be 85 cm, a judging standard value for the abdominal girth $W_L$ of female subjects is defined in advance to be 85 cm, and obesity of the subject is judged based on comparison of each of values of the abdominal girth $W_L$, the Body Mass Index (BMI), and the abdominal visceral fat cross sectional area VA with each of the pre-defined judging standard value.

16. A visceral fat determining device with a weight-measuring function comprising:

weight-measuring means for measuring a weight of a subject when the subject stands on a measuring surface;

input means for inputting personal data, including an abdominal girth $W_L$, that is a circumferential length of a torso of the subject, height, sex, and age of the subject;

a data processing unit that stores the personal data and calculates an estimated value of an abdominal visceral fat cross-sectional area VA of the subject based on the personal data;

a display portion that displays the personal data and a result of the calculation performed by the data processing unit; and body-fat ratio measuring means for measuring a human body impedance Z of the subject through electrodes in contact with terminals of the subject's body and for obtaining a body-fat ratio FAT of the subject based on the measured body impedance Z and the inputted personal data or part of the data, wherein the data processing unit stores a third regression coefficient of the abdominal girth $W_L$, a first regression coefficient of the body-fat ratio FAT, and a third regression constant which are obtained based on statistical analysis of correlation between actually measured values of the abdominal visceral fat cross-sectional area VA obtained in abdominal tomography of human bodies of random samples and values of the abdominal girth $W_L$ of the human samples and values of the body-fat ratio FAT of the human samples and the estimated value of the abdominal visceral fat cross-sectional area VA of the subject is obtained based on a value of the abdominal girth $W_L$, a value of the body-fat ratio FAT obtained with the body-fat ratio measuring means, the third regression coefficient of the abdominal girth $W_L$, the first regression coefficient of the body fat ratio FAT, and the third regression constant.

17. A visceral fat determining device with a weight-measuring function comprising:

weight-measuring means for measuring a weight of a subject when the subject stands on a measuring surface;

input means for inputting personal data including an abdominal girth $W_L$ that is a circumferential length of a torso of the subject, height, and a thickness of abdominal subcutaneous fat s of the subject;

a data processing unit that stores the personal data and calculates an estimated value of an abdominal visceral fat cross-sectional area VA of the subject based on the personal data; and a display portion that displays the personal data and a result of the calculation performed by the data processing unit, wherein the data processing unit stores a fourth regression coefficient of the abdominal girth $W_L$, a second regression coefficient of Body Mass Index (BMI), a first regression coefficient of the thickness of abdominal subcutaneous fat s, and a fourth regression constant which are obtained based on statistical analysis of a correlation between actually measured values of the abdominal visceral fat cross sectional area VA obtained in abdominal tomography of human bodies of random samples and values of the Body Mass Index (BMI) related to a level of obesity of the human samples and values of the thickness of the abdominal subcutaneous fat s of the human samples and the estimated value of the abdominal visceral fat cross-sectional area VA of the subject is obtained based on a value of the abdominal girth $W_L$, a value of the Body Mass Index (BMI), a value of the thickness of abdominal subcutaneous fat s, the fourth regression coefficient of the abdominal girth $W_L$, the second regression coefficient of the Body Mass Index (BMI), the first regression coefficient of the thickness of abdominal subcutaneous fat s, and the fourth regression constant.

18. A visceral fat determining device with a weight-measuring function comprising:

weight-measuring means for measuring a weight of a subject when the subject stands on a measuring surface;

input means for inputting personal data including an abdominal girth $W_L$ that is a circumferential length of a torso of the subject, height, and a thickness of abdominal subcutaneous fat s of the subject;

a data processing unit that stores the personal data and calculates an estimated value of an abdominal visceral fat cross-sectional area VA of the subject based on the personal data; and a display portion that displays the personal data and a result of the calculation performed by the data processing unit, wherein the data processing unit stores a fourth regression coefficient of the abdominal girth $W_L$, a second regression coefficient of Body Mass Index (BMI), a first regression coefficient of the thickness of abdominal subcutaneous fat s, and a fourth regression constant which are obtained based on statistical analysis of a correlation between actually measured values of the abdominal visceral fat cross-sectional area VA obtained in abdominal tomography of human bodies of random samples and values of the Body Mass Index (BMI) related to the level of the obesity of the human samples and values of the thickness of the abdominal subcutaneous fat s of the human samples, the estimated value of the abdominal visceral fat cross-sectional area VA of the subject is obtained based on a value of the abdominal girth $W_L$, a value of the Body Mass Index (BMI), a value of the thickness of abdominal subcutaneous fat s, the fourth regression coefficient of the abdominal girth $W_L$, the second regression coefficient of the Body Mass Index (BMI), the first regression coefficient of the thickness of abdominal subcutaneous fat s, and the fourth regression constant, and an abdominal subcutaneous fat cross-sectional area SA of the subject is further obtained based on a value of the thickness of the abdominal subcutaneous fat s and a value of the abdominal girth $W_L$.

19. The visceral fat determining device with a weight-measuring function according to claim 18, wherein a ratio of the estimated value of an abdominal visceral fat cross-sectional area VA to the abdominal subcutaneous fat cross-sectional area SA, VSR, is further obtained.

20. The visceral fat determining device with a weight-measuring function according to claim 18, wherein a total abdominal fat cross-sectional area WA is further obtained based on the estimated value of the abdominal visceral fat cross-sectional area VA and the abdominal subcutaneous fat cross-sectional area SA.

21. A visceral fat determining device with a weight-measuring function comprising:

weight-measuring means for measuring a weight of a subject when the subject stands on a measuring surface;

input means for inputting personal data including an abdominal girth $W_L$ that is a circumferential length of a torso of the subject, and a height, sex, age, and a thickness of abdominal subcutaneous fat s of the subject;

a data processing unit that stores the personal data and calculates an estimated value of an abdominal visceral fat cross-sectional area VA of the subject based on the personal data;

a display portion that displays the personal data and a result of the calculation performed by the data processing unit; and body fat ratio measuring means for measuring a human body impedance Z of the subject through electrodes in contact with terminals of the subject's body and for obtaining a body-fat ratio FAT of the subject based on the measured body impedance Z and the inputted personal data or part of the data, wherein the data processing unit stores a fifth regression coefficient of the abdominal girth $W_L$, a second regression coefficient of the body fat ratio FAT, a second regression coefficient of the thickness of abdominal subcutaneous fat s, and a fifth regression constant which are obtained based on statistical analysis of a correlation between actually measured values of the abdominal visceral fat cross-sectional area VA obtained in abdominal tomography of human bodies of random samples and values of the abdominal girth $W_L$ of the human samples, values of the body fat ratio FAT of the human samples, and values of the thickness of abdominal subcutaneous fat s and the estimated value of an abdominal visceral fat cross-sectional area VA of the subject is obtained based on a value of the abdominal girth $W_L$, a value of the body-fat ratio FAT obtained with the body-fat ratio measuring means, a value of the thickness of abdominal subcutaneous fat s, the fifth regression coefficient of the abdominal girth $W_L$, the second regression coefficient of the body-fat ratio FAT, and the second regression coefficient of the thickness of abdominal subcutaneous fat s, and the fifth regression constant.

22. A visceral fat determining device with a weight-measuring function comprising:

weight-measuring means for measuring a weight of a subject when the subject stands on a measuring surface;

input means for inputting personal data including an abdominal girth $W_L$ that is a circumferential length of a torso of the subject, and a height, sex, age, and a thickness of abdominal subcutaneous fat s of the subject;

a data processing unit that stores the personal data and calculates an estimated value of an abdominal visceral fat cross-sectional area VA of the subject based on the personal data;

a display portion that displays the personal data and a result of the calculation performed by the data processing unit; and body-fat ratio measuring means for measuring a human body impedance Z of the subject through electrodes in contact with terminals of the subject's body and for obtaining a body-fat ratio FAT of the subject based on the measured body impedance Z and the inputted personal data or part of the data, wherein the data processing unit stores a fifth regression coefficient of the abdominal girth $W_L$, a second regression coefficient of the body-fat ratio FAT, a second regression coefficient of the thickness of abdominal subcutaneous fat s, and a fifth regression constant which are obtained based on statistical analysis of correlation between actually measured values of the abdominal visceral fat cross-sectional area VA obtained in abdominal tomography of human bodies of random samples and values of the abdominal girth $W_L$ of the human samples, values of the body-fat ratio FAT of the human samples, and values of the thickness of abdominal subcutaneous fat s, the estimated value of an abdominal visceral fat cross-sectional area VA of the subject is obtained based on a value of the abdominal girth $W_L$, a value of the body-fat ratio FAT obtained with the body-fat ratio measuring means, a value of the thickness of abdominal subcutaneous fat s, the fifth regression coefficient of the abdominal girth $W_L$, the second regression coefficient of the body-fat ratio FAT, the second regression coefficient of the thickness of abdominal subcutaneous fat s, and the fifth regression constant, and an abdominal subcutaneous fat cross-sectional area SA of the subject is further obtained based on a value of the thickness of the abdominal subcutaneous fat s and a value of the abdominal girth $W_L$.

23. The visceral fat determining device with a weight-measuring function according to claim 22, wherein a ratio of the estimated value of the abdominal visceral fat cross-sectional area VA to the value of the abdominal subcutaneous fat cross-sectional area SA, VSR, is further obtained.

24. The visceral fat determining device with a weight-measuring function according to claim 22, wherein a total abdominal fat cross-sectional area WA is further obtained based on the estimated value of the abdominal visceral fat cross-sectional area VA and the value of the abdominal subcutaneous fat cross-sectional area SA.

25. A visceral fat determining device with a weight-measuring function comprising:

weight-measuring means for measuring a weight of a subject when the subject stands on a measuring surface;

input means for inputting personal data including an abdominal girth $W_L$ that is a circumferential length of a torso of the subject and a height of the subject;

a data processing unit that stores the personal data and calculates an estimated value of an abdominal visceral fat cross-sectional area VA of the subject based on the personal data; and a display portion that displays the personal data and a result of the calculation performed by the data processing unit, wherein the data processing unit stores a first regression coefficient of a first abdominal girth index and a sixth regression constant which are obtained based on statistical analysis of a correlation between actually measured values of the abdominal visceral fat cross-sectional area VA obtained in abdominal tomography of human bodies of random samples and values of the first abdominal girth index obtained by dividing a square of the abdominal girth $W_L$ by the height of the subject and the estimated value of the abdominal visceral fat cross-sectional area VA of the subject is obtained based on a value of the first abdominal girth index, the first regression coefficient of the first abdominal girth index, and the sixth regression constant.

26. A visceral fat determining device with a weight-measuring function comprising:

weight-measuring means for measuring a weight of a subject when the subject stands on a measuring surface;

input means for inputting personal data including an abdominal girth $W_L$ that is a circumferential length of a torso of the subject, and a height, sex, and age of the subject;

a data processing unit that stores the personal data and calculates an estimated value of an abdominal visceral fat cross-sectional area VA of the subject based on the personal data; and a display portion that displays the personal data and a result of the calculation performed by the data processing unit, and body-fat ratio measuring means for measuring a human body impedance Z of the subject through electrodes in contact with feet of the subject as terminals of the subject's body and for calculating a body-fat ratio FAT of the subject based on the measured body impedance Z and the inputted personal data or part of the data, wherein the data processing unit stores a sixth regression coefficient of the abdominal girth $W_L$, a third regression coefficient of Body Mass Index (BMI), a third regression coefficient of the body fat ratio FAT, and a ninth regression constant which are obtained based on statistical analysis of a correlation between actually measured values of the abdominal visceral fat cross-sectional area VA obtained in abdominal tomography of human bodies of random samples and values of the Body Mass Index (BMI) of the human samples and values of the of the body-fat ratio FAT of the human samples and the estimated value of the abdominal visceral fat cross-sectional area VA of the subject is obtained based on a value of the abdominal girth $W_L$, a value of the Body Mass Index (BMI), a value of the body fat ratio FAT, the sixth regression coefficient of the abdominal girth $W_L$, the third regression coefficient of the Body Mass Index (BMI), the third regression coefficient of the body-fat ratio FAT, and the ninth regression constant.

27. A visceral fat determining device with a weight-measuring function comprising:

weight-measuring means for measuring a weight of a subject when the subject stands on a measuring surface;

input means for inputting personal data including an abdominal girth $W_L$ that is a circumferential length of a torso of the subject, and a height, sex, age, and a thickness of abdominal subcutaneous fat s of the subject;

a data processing unit that stores the personal data and calculates an estimated value of an abdominal visceral fat cross-sectional area VA of the subject based on the personal data; and a display portion that displays the personal data and a result of the calculation performed by the data processing unit, and body-fat ratio measuring means for measuring a human body impedance Z of the subject through electrodes in contact with feet of the subject as terminals of the subject's body and for calculating a body-fat ratio FAT of the subject based on the measured body impedance Z and the inputted personal data or part of the data, wherein the data processing unit stores a seventh regression coefficient of the abdominal girth $W_L$, a fourth regression coefficient of Body Mass Index (BMI), a fourth regression coefficient of the body fat ratio FAT, a third regression coefficient of the thickness of abdominal subcutaneous fat s, and a tenth regression constant which are obtained based on statistical analysis of a correlation between actually measured values of the abdominal visceral fat cross-sectional area VA obtained in abdominal tomography of human bodies of random samples and values of the Body Mass Index (BMI) of the human samples, values of the body-fat ratio FAT of the human samples, and values of the thickness of abdominal subcutaneous fat s of the human samples and the estimated value of the abdominal visceral fat cross-sectional area VA of the subject is obtained based on a value of the abdominal girth $W_L$, a value of the Body Mass Index (BMI), a value of the body-fat ratio FAT, a value of the thickness of abdominal subcutaneous fat s, the seventh regression coefficient of the abdominal girth $W_L$, the fourth regression coefficient of the Body Mass Index (BMI), the fourth regression coefficient of the body fat-ratio FAT, the third regression coefficient of the thickness of abdominal subcutaneous fat s, and the tenth regression constant.

28. A visceral fat determining with a weight-measuring function comprising:

weight-measuring means for measuring a weight of a subject when the subject stands on a measuring surface;

input means for inputting personal data including an abdominal girth $W_L$ that is a circumferential length of a torso of the subject and a height of the subject;

a data processing unit that stores the personal data and calculates an estimated value of an abdominal visceral fat cross-sectional area VA of the subject based on the personal data;

a display portion that displays the personal data and a result of the calculation performed by the data processing unit; and impedance-measuring means for measuring a human body impedance Z of the subject through electrodes in contact with terminals of the subject's body, wherein the data processing unit stores an eighth regression coefficient of the abdominal girth $W_L$, a first regression coefficient of a term $(T_L^2/Z)$, and an eleventh regression constant which are obtained based on statistical analysis of a correlation between the actually measured values of the abdominal visceral fat cross-sectional area VA obtained in abdominal tomography of human bodies of random samples and values of the abdominal girth $W_L$ of the human samples and values of the term $(T_L^2/Z)$ of the human samples obtained by dividing a square of the height $T_L$ by the body impedance Z and the estimated value of the abdominal visceral fat cross-sectional area VA of the subject is obtained based on a value of the abdominal girth $W_L$, a value of the body impedance Z measured with the impedance measuring means, a value of the height $T_L$ obtained through the input means, the eighth regression coefficient of the abdominal girth $W_L$, the first regression coefficient of the term $(T_L^2/Z)$, and the eleventh regression constant.

29. A visceral fat determining device with a weight-measuring function comprising:

weight-measuring means for measuring a weight of a subject when the subject stands on a measuring surface;

input means for inputting personal data including an abdominal girth $W_L$ that is a circumferential length of a torso of the subject and a height of the subject;

a data processing unit that stores the personal data and calculates an estimated value of an abdominal visceral fat cross-sectional area VA of the subject based on the personal data;

a display portion that displays the personal data and a result of the calculation performed by the data processing unit; and impedance-measuring means for measuring a human body impedance Z of the subject through electrodes in contact with terminals of the subject's body, wherein the data processing unit stores a ninth regression coefficient of the abdominal girth $W_L$, a first regression coefficient of the human body impedance Z, and a twelfth regression constant which are obtained based on statistical analysis of a correlation between the actually measured values of the abdominal visceral fat cross-sectional area VA obtained in abdominal tomography of human bodies of random samples and values of the abdominal girth $W_L$ of the human samples and values of the body impedance Z of the human samples and the estimated value of the abdominal visceral fat cross-sectional area VA of the subject is obtained based on a value of the abdominal girth $W_L$, a value of the body impedance Z measured with the impedance measuring means, the ninth regression coefficient of the abdominal girth $W_L$, the first regression coefficient of the body impedance Z, and the twelfth regression constant.

30. A visceral fat determining device with a weight-measuring function comprising:

weight-measuring means for measuring a weight of a subject when the subject stands on a measuring surface;

input means for inputting personal data including an abdominal girth $W_L$ that is a circumferential length of a torso of the subject, and a height, weight, sex, and age of the subject;

a data processing unit that stores the personal data and calculates an estimated value of an abdominal visceral fat cross-sectional area VA of the subject based on the personal data;

a display portion that displays the personal data and a result of the calculation performed by the data processing unit; and body-fat ratio measuring means for measuring a human body impedance Z of the subject through electrodes in contact with terminals of the subject's body and for obtaining a body-fat ratio FAT of the subject based on the measured body impedance Z and the inputted personal data or part of the data, wherein the data processing unit stores a first regression coefficient of a term $(W_L^2 \cdot T_L \cdot age)$, a first regression coefficient of a term $(W_L^2 \cdot T_L \cdot FAT)$ and a thirteenth regression constant which are obtained based on statistical analysis of a correlation between the actually measured values of the abdominal visceral fat cross-sectional area VA obtained in abdominal tomography of human bodies of random male samples and values of the term $(W_L^2 \cdot T_L \cdot age)$ obtained by multiplying a square of the abdominal girth $W_L^2$ of the human male samples, the height $T_L$ of the human male samples, and the age of the human male samples and values of the term $(W_L^2 \cdot T_L \cdot FAT)$ obtained by multiplying a square of the abdominal girth $W_L^2$ of the human male samples, the height $T_L$ of the human male samples, and the body fat ratio FAT of the human male samples and when inputted subject's personal data of sex is "male," the estimated value of the abdominal visceral fat cross-sectional area VA of the subject is obtained based on a value of the abdominal girth $W_L$ of the subject, a value of the age of the subject inputted through the input means, a value of the body-fat ratio FAT of the subject measured with the body-fat ratio measuring means, the first regression coefficient of the term $(W_L^2 \cdot T_L \cdot age)$, the first regression coefficient of the term $(W_L^2 \cdot T_L \cdot FAT)$, and the thirteenth regression constant.

31. A visceral fat determining device with a weight-measuring function comprising:

weight-measuring means for measuring a weight of a subject when the subject stands on a measuring surface;

input means for inputting personal data including an abdominal girth $W_L$ that is a circumferential length of a torso of the subject, and a height, weight, sex, and age of the subject;

a data processing unit that stores the personal data and calculates an estimated value of an abdominal visceral fat cross-sectional area VA of the subject based on the personal data;

a display portion that displays the personal data and a result of the calculation performed by the data processing unit; and body-fat ratio measuring means for measuring a human body impedance Z of the subject through electrodes in contact with terminals of the subject's body and for obtaining a body-fat ratio FAT of the subject based on the measured body impedance Z and the inputted personal data or part of the data, wherein the data processing unit stores a second regression coefficient of the term $(W_L^2 \cdot T_L \cdot age)$, a fifth regression coefficient of the body fat ratio FAT, and a fourteenth regression constant which are obtained based on statistical analysis of a correlation between the actually measured values of the abdominal visceral fat cross-sectional area VA obtained in abdominal tomography of human bodies of random female samples and values of the term $(W_L^2 \cdot T_L \cdot age)$ obtained by multiplying a square of the abdominal girth $W_L^2$ of the human female samples, the height $T_L$ of the human female samples, and the age of the human female samples and values of the body fat ratio FAT of the human female samples and when inputted subject's personal data of sex is "female," the estimated value of the abdominal visceral fat cross-sectional area VA of the subject is obtained based on a value of the abdominal girth $W_L$ of the subject, a value of the age of the subject inputted through the input means, a value the body-fat ratio FAT of the subject measured with the body-fat ratio measuring means, the second regression coefficient of the term $(W_L^2 \cdot T_L \cdot age)$, the fifth regression coefficient of the body fat ratio FAT, and the fourteenth regression constant.

* * * * *